United States Patent [19]

Bokoch et al.

[11] Patent Number: 5,726,155
[45] Date of Patent: Mar. 10, 1998

[54] REGULATION OF OXIDATIVE BURST USING LMWG-DERIVED PEPTIDES AND ANALOGS

[75] Inventors: Gary M. Bokoch, Encinitas; John T. Curnutte, Hillsborough, both of Calif.

[73] Assignee: The Scripps Research Institute, La Jolla, Calif.

[21] Appl. No.: 156,552

[22] Filed: Nov. 15, 1993

Related U.S. Application Data

[63] Continuation-in-part of Ser. No. 102,944, Aug. 2, 1993, abandoned.

[51] Int. Cl.$^6$ .......................... A61K 38/00; C07K 5/00; C07K 7/00; C07K 17/00
[52] U.S. Cl. .................. 514/13; 514/14; 514/15; 514/16; 514/17; 530/326; 530/327; 530/328; 530/329
[58] Field of Search .................. 514/12–17, 324, 514/326, 327, 328, 329

[56] References Cited

U.S. PATENT DOCUMENTS 5,244,916  9/1993  Bokoch .................................. 514/460
5,519,116  5/1996  Wagner et al. .......................... 530/327

FOREIGN PATENT DOCUMENTS 9303749  3/1993  WIPO .

OTHER PUBLICATIONS

Aviram, et al., "Lovastatin Inhibits Low–Density Lipoprotein Oxidation and Alters Its Fluidity and Uptake by Macrophages: In Vitro and In Vivo Studies", (Abstract), *Metab*.41(3): 229–35 (March 1992).
Leusen, et al., "A Point Mutation in gp91–phox of Cytochrome b$_{558}$ of the Human NADPH Oxidase Leading to Defective Translocation of the Cytosolic Proteins p47–phox and p67–phox", *J. Clin. Invest.*, 93: 2120–2126 (1994).
Maridonneau–Parini, et al., "Heat Shock in Human Neutrophils: Superoxide Generation is Inhibited by a Mechanism Distinct From Heat–Denaturation of NADPH Oxidase and is Protected by Heat Shock Proteins in Thermotolerant Cells", (*Jnl. of Cellular Physiology*) 156: 204–211 (1993).
Newburger, et al., "Chronic Granulomatous Disease and Glutathione Peroxidase Deficiency, Revisited", *Blood* 84: 3861–3869 (1994).
Zeller, et al., "C–Reactive Protein Selectively Enhances the Intracellular Generation of Reactive Oxygen Products by IgG–Stimulated Monocytes and Neutrophils", (*J. Leukocyte Biology*) 52: 449–455 (1992).

Summers, et al., *Texas Agr. Exp. Station Bulletin*: 1555: pp. (1988).
Settleman, et al., *Nature* 359: 153–4 (1992).
Hart, et al., *J. Biol. Chem.* 266: 20840–20848 (1991).
Diekmann, et al., *Nature* 351: 400–402 (1991).
Bokoch and Der, *FASEB J.* 7: 750–759 (1993).
Hall, *Cell* 69: 389–391 (1992).
Ellis, et al., *Nature* 343: 377–381 (1990).
Dibsbury et al. J. Biol Chem vol. 264 p. 16378 (1989) see attached search report.
Touchot et al. PNAS vol. 84 p. 8210 (1987) see search report.
Norgaver et al., Biochem J. vol. 282 p. 393 (1992).
Hirai et al., Chem. Pharm. Bull. vol. 27 p. 1942 (1979) see attached search report.
Hirai et al. Biomed Res. vol. 1 p. 185 (1980) see attached search report.
Hirai et al., Chem. Pharm Bull. vol. 27 p.1945 (1979) see attached search report.
Oberhauser et al. Nature vol. 360 p. 270 (1992).
Richmond et al. FEBS Lett. vol. 326 P. 124 (1993).
Carter et al., J. Cell Biol. vol. 120 p. 37 (1993).
Hall, Nature vol.249 P. 635 (1990).
Eklund et al., J. Biol. Chem. vol. 266 p. 13964 (1991).
Kahn et al., J. Biol. Chem. vol. 259 p. 6228 (1984).
Knaus et al., Science vol. 254 p. 1512 (1991).
Bokoch et al., Science vol. 254 p. 1794 (1991).

*Primary Examiner*—Sheela Huff
*Attorney, Agent, or Firm*—Thomas Fitting; Emily Holmes

[57] ABSTRACT

The present invention relates to optionally substituted, non-toxic peptides and derivatives capable of inhibiting superoxide production in phagocytic cells. The invention also relates to compositions and methods useful in inhibiting inflammation and in treating inflammatory disorders such as autoimmune disorders, gout, adult respiratory distress syndrome, asthma, myocardial infarction, and various dermatological disorders.

The present invention contemplates compositions derived from low molecular weight GTP-binding proteins (LMWG), mastoparan, GAP proteins, and related peptides. The invention further contemplates compositions useful in inhibiting activation of NADPH oxidase or in promoting GDP/GTP exchange. Therapeutic compositions containing various inhibitors, and methods of using same, are also disclosed.

3 Claims, 8 Drawing Sheets

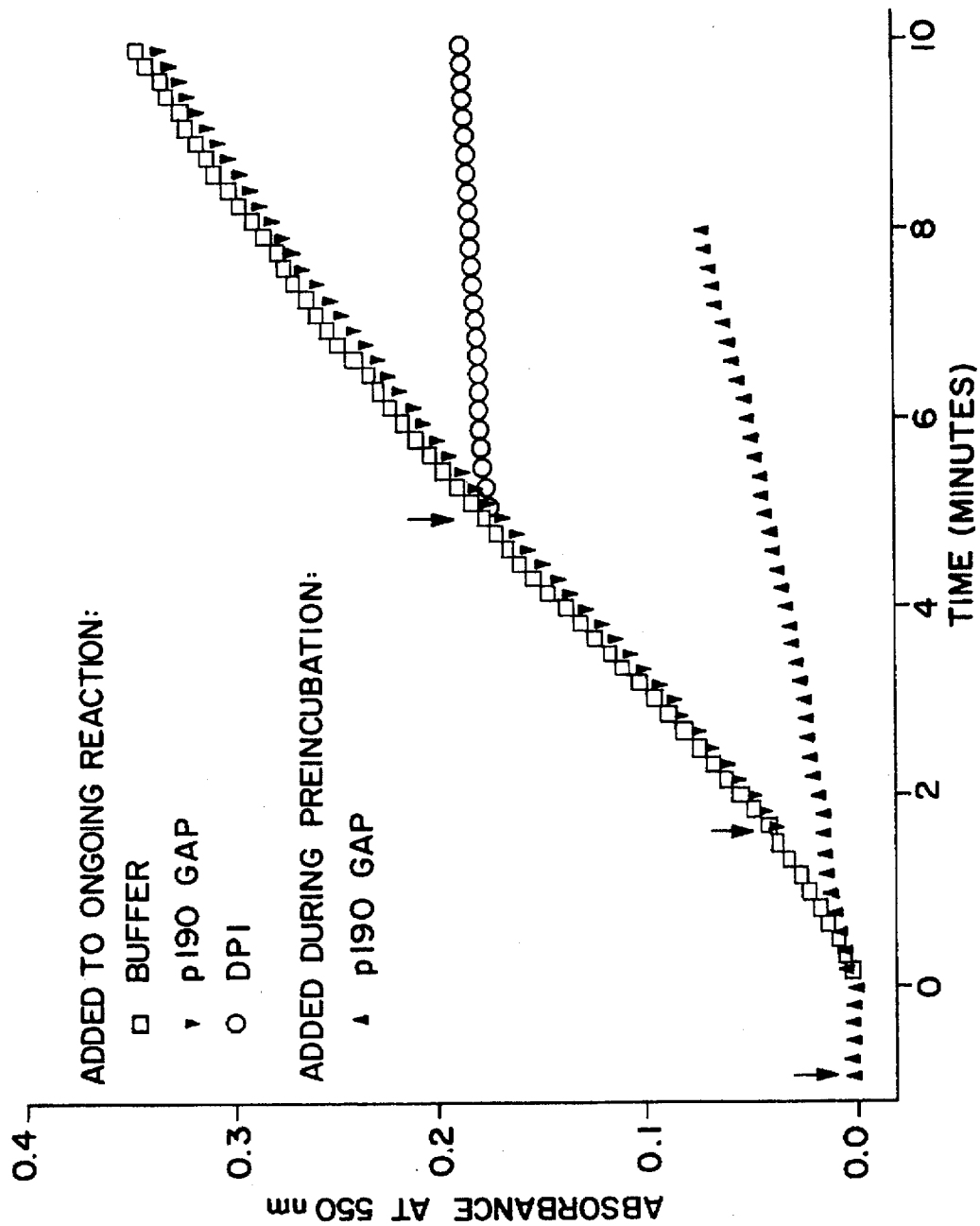

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 14
        ( D ) OTHER INFORMATION: /label= - NH2

( x i ) SEQUENCE DESCRIPTION: SEQ ID NO:1:

```
Ile Asn Leu Lys Ala Leu Ala Ala Leu Ala Lys Lys Ile Leu
 1               5                   10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 14
        ( D ) OTHER INFORMATION: /label= - NH2

( x i ) SEQUENCE DESCRIPTION: SEQ ID NO:2:

```
Ile Asn Leu Lys Ala Leu Ala Ala Leu Ala Lys Ala Leu Leu
 1               5                   10
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 12
        ( D ) OTHER INFORMATION: /label= - NH2

( x i ) SEQUENCE DESCRIPTION: SEQ ID NO:3:

```
     Leu  Lys  Ala  Leu  Ala  Ala  Leu  Ala  Lys  Lys  Ile  Leu
     1                   5                        10
```

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 14
        ( D ) OTHER INFORMATION: /label= - NH2

( x i ) SEQUENCE DESCRIPTION: SEQ ID NO:4:

```
     Ile  Asn  Trp  Lys  Gly  Ile  Ala  Ala  Met  Ala  Lys  Lys  Leu  Leu
     1                   5                        10
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 14
        ( D ) OTHER INFORMATION: /label= - NH2

( x i ) SEQUENCE DESCRIPTION: SEQ ID NO:5:

```
     Val  Asp  Trp  Lys  Lys  Ile  Gly  Gln  His  Ile  Leu  Ser  Val  Leu
     1                   5                        10
```

( 2 ) INFORMATION FOR SEQ ID NO:6:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
     Gly  Leu  Ala  Gln  Lys  Leu  Leu  Glu  Ala  Leu  Gln  Lys  Ala  Leu  Leu  Ala
     1                   5                        10                       15
```

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
     Gly  Asn  Ile  Phe  Ala  Asn  Leu  Phe  Lys  Gly  Leu  Phe  Gly  Lys  Lys  Glu
     1                   5                        10                       15
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Gly Leu Thr Ile Ser Ser Leu Phe Ser Arg Leu Phe Gly Lys Lys Gln
    1               5                   10                  15

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Thr Ile Ser Ser Leu Phe Ser Arg Leu Phe Gly Lys Lys Gln
    1               5                   10

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Ser Ser Leu Phe Ser Arg Leu Phe Gly Lys Lys Gln
    1               5                   10

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

Cys Pro Pro Pro Val Lys Lys Arg Lys Arg Lys
    1               5                   10

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Cys Pro Gln Pro Thr Arg Gln Gln Lys Arg Ala
    1               5                   10

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
        Pro   Gly   Lys   Ala   Arg   Lys   Lys   Ser   Ser
        1                       5
```

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
        Glu   Lys   Lys   Lys   Pro   Lys   Lys   Lys   Ser
        1                       5
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
        Val   Ser   Ala   Leu   Gly   Ile   Asp   Phe   Lys   Val   Lys   Thr   Ile   Tyr   Arg   Asn
        1                       5                             10                            15
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
        Leu   Thr   Gln   Arg   Gly   Leu   Lys   Thr   Val   Phe   Asp   Glu
        1                       5                             10
```

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
        Glu   Lys   Leu   Lys   Glu   Lys   Lys   Leu   Thr   Pro   Ile
        1                       5                             10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
        Ser   Lys   Phe   Glu   Asp   Leu   Asn   Lys   Arg   Lys   Asp   Thr
        1                       5                             10
```

( 2 ) INFORMATION FOR SEQ ID NO:19:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( x i ) SEQUENCE DESCRIPTION: SEQ ID NO:19:

Met Gly Cys Thr Val Ser Ala Glu Asp Lys Ala Ala Ala Glu Arg
1               5               10                  15

( 2 ) INFORMATION FOR SEQ ID NO:20:

( i ) SEQUENCE CHARACTERISTICS:
    ( A ) LENGTH: 22 amino acids
    ( B ) TYPE: amino acid
    ( D ) TOPOLOGY: linear ( i i ) MOLECULE TYPE: protein ( x i ) SEQUENCE DESCRIPTION: SEQ ID NO:20:

Lys Asn Val Phe Asp Glu Ala Ile Leu Ala Ala Leu Glu Pro Pro Glu
1               5               10                  15

Pro Lys Lys Ser Arg Arg
            20

( 2 ) INFORMATION FOR SEQ ID NO:21:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( i x ) FEATURE:
    ( A ) NAME/KEY: Region
    ( B ) LOCATION: one-of(7)
    ( D ) OTHER INFORMATION: /label=Xaa
        / note= "Xaa at each specified amino acid residue
        position is either G,S, T, C, N, Q, D, E, or H
        single letter amino acid residue."

( x i ) SEQUENCE DESCRIPTION: SEQ ID NO:21:

Gly Xaa Xaa Xaa Xaa Leu Phe Xaa Xaa Leu Phe Gly Lys Lys Xaa
1               5               10                  15

( 2 ) INFORMATION FOR SEQ ID NO:22:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( x i ) SEQUENCE DESCRIPTION: SEQ ID NO:22:

Gly Glu Leu Ala Gln Lys Leu Glu Gln Ala Leu Gln Lys Leu Ala
1               5               10                  15

( 2 ) INFORMATION FOR SEQ ID NO:23:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( x i ) SEQUENCE DESCRIPTION: SEQ ID NO:23:

```
Gly Glu His Ala Gln Lys His Glu Gln Ala Leu Gln Lys Leu Ala
1               5                   10                  15
```

(2) INFORMATION FOR SEQ ID NO:24:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:24:

```
Met Glu Glu Glu Glu Tyr Met Pro Met Glu
1               5                   10
```

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: protein (ix) FEATURE:
        (A) NAME/KEY: Modified-site
        (B) LOCATION: 4
        (D) OTHER INFORMATION: /label=Xaa
            / note= '"Xaa is Nle'"

(ix) FEATURE:
        (A) NAME/KEY: Modified-site
        (B) LOCATION: 1
        (D) OTHER INFORMATION: /label= -N- CHO (xi) SEQUENCE DESCRIPTION: SEQ ID NO:25:

```
Xaa Leu Phe Xaa Tyr Lys
1               5
```

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GGGGGAAGCT TCATATGCAG GCCATCAAGT GTG        33

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGGGGGGGAT CCTAGAGGAG GCTGCAGGCG CG        32

(2) INFORMATION FOR SEQ ID NO:28:

(i) SEQUENCE CHARACTERISTICS:
        (A) LENGTH: 61 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

GGGGGGGGTA CCATGGAGGA GGAGGAGTAC ATGCCGATGG AGCAGGCCAT CAAGTGTGTG    60

G    61

(2) INFORMATION FOR SEQ ID NO:29:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

GGGGGGGGAT CCTAGAGGAG GCTGCAGGCG CG    32

(2) INFORMATION FOR SEQ ID NO:30:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:30:

CGAAGGATCC GGAACTTCGA TGACCAGC    28

(2) INFORMATION FOR SEQ ID NO:31:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:31:

CGGAATTCTA TTTAGCATCC AGCTCCAG    28

REGULATION OF OXIDATIVE BURST USING LMWG-DERIVED PEPTIDES AND ANALOGS

CROSS REFERENCE TO RELATED APPLICATION

This is a continuation-in-part of U.S. patent application Ser. No. 08/102,944, filed Aug. 2, 1993, now abandoned, the disclosures of which are hereby incorporated by reference.

This invention was supported in part by National Institutes of Health Contract HL 48008. The government has certain rights in the invention.

TECHNICAL FIELD

This invention relates to the use of GTP-binding proteins, particularly low molecular weight GTP-binding proteins (LMWG), analogs, and peptides derived therefrom to inhibit activation of NADPH oxidase and other enzyme systems involved in the oxidative burst of phagocytic cells.

BACKGROUND OF THE INVENTION

Neutrophils (polymorphonuclear leukocytes) and macrophages play a major role in the body's defense against harmful foreign pathogens. In the course of serving this function, phagocytes must respond to a variety of inflammatory stimulants, including N-formylated peptides, complement component C5a, leukotriene $B_4$, platelet-activating factor, and interleukin 8 (see, e.g., Becker, *J. Leukocyte Biol.* 47: 378–389 (1990)).

Phagocytes have specific cell surface receptors for these factors that are coupled to the intracellular environment through oligomeric GTP-binding proteins, which are also known as G proteins. These transducing elements are found in all cells and couple ligand-activated receptors to the intracellular second messenger cascades (Birnbaumer, et al., *CRC Crit. Rev. Biochem. Mol. Biol.* 25: 225–244 (1990)). Protein purification and molecular cloning have revealed the existence of multiple additional G proteins that bear homology with the ras oncogene products (Der, in *Oncogenes*, Benz & Liu (eds), Kluweer Academic, Boston, Mass., 1989, pp. 73–119; Hall, *Science* 249: 635–640 (1990)). These smaller monomeric proteins are referred to herein as low molecular weight GTP-binding proteins (LMWGs). Recent findings have implicated the LMWGs in a variety of neutrophil activities.

One of these activities is the eradication of disease-causing organisms. For example, the phagocytic cell NADPH oxidase generates superoxide anion ($O_2^-$) as a means to destroy ingested microorganisms. Its importance in bacterial killing is evidenced by the chronic infections and even death observed in patients with severe neutropenia, chronic granulomatous disease, and other disorders of neutrophil function. However, the inappropriate or excessive formation of $O_2^-$ and its byproducts can both initiate and exacerbate inflammation. Inflammatory diseases and/or secondary inflammation resulting from a primary disorder are serious health problems. Therefore, the development of means to intervene in this process in a specific manner is of great therapeutic interest.

Human neutrophils and other phagocytic cells undergo a respiratory burst in which superoxide anion ($O_2^-$) and its metabolites—hydrogen peroxide ($H_2O_2$), hypochlorous and other hypohalous acids, and hydroxyl radical (OH)—are produced as a means of destroying ingested microorganisms. The significance of the respiratory burst in host defense is made evident by the recurrent and life-threatening infections that occur in patients with chronic granulomatous disease (CGD) in whose phagocytes the burst does not occur. It is known that CGD results from genetic defects in any one of four known protein components of the NADPH oxidase enzyme responsible for generating $O_2^-$ (see J. T. Curnutte, in *Phagocytic Defects II: Abnormalities of the Respiratory Burst* (vol. 2), J. T. Curnutte (ed.), Saunders, Philadelphia, pp. 241–252 (1988)). Studies with various cell-free oxidase activation systems (Curnutte, et al., *J. Biol. Chem.* 262: 450 (1987); Bromberg, et al., *J. Biol. Chem.* 220: 13539 (1985)) and cellular material from CGD patients have helped to determine the identity and function of the components of the NADPH oxidase. The oxidase is composed of membrane-bound proteins that include cytochrome $b_{558}$ and possibly a 45 kD flavoprotein, as well as cytosolic components, of which two have been characterized: p47 $_{[phox]}$ and p67 $_{[phox]}$ (Clark, *J. Infect. Dis.* 161: 1140 (1990); Smith and Curnutte, *Blood* 77: 673 (1991)). The NADPH oxidase is activated at least in part by the association of these components into a membrane-bound complex that can transfer electrons from NADPH to molecular oxygen, generating $O_2^-$ (Clark, Id.; Smith and Curnutte, Id.).

GTP-binding proteins have recently been implicated in the regulation of NADPH oxidase activity. GTP appears to be required for oxidase activation in cell-free systems and GDP analogs inhibit this activation. (See, e.g., Gabig, et al., *J. Biol. Chem.* 262: 1685 (1987); Seifert, et al., *FEBS Lett.* 205: 161 (1986); Uhlinger, et al., *J. Biol. Chem.* 266: 20990–997 (1991); Pereri, et al., *PNAS USA* 89: 2494–98 (1992).) It has also been observed that inhibition of protein isoprenylation decreases the rate of $O_2^-$ generation. (See, e.g., Knaus, et al., *Science* 254: 1512–1515 (1991); Bokoch and Prossnitz, *J. Clin. Invest.* 89: 402–408 (1992)); and Chuang, et al., *J. Biol. Chem.* 268: 775–778 (1993).)

NADPH oxidase can be activated in cell-free systems containing cytosol and membranes from unstimulated phagocytes by the addition of an anionic amphiphile such as arachidonate or sodium dodecyl sulfate (SDS). (See, e.g., Curnutte, *J. Clin. Invest.* 75: 1740–1743 (1985); Bromberg and Pick, *Cell. Immunol.* 88: 213–221 (1984); McPhail, et al., *J. Clin. Invest.* 75: 1735–1739 (1985).) Several reports have shown that GTP or one of its non-hydrolyzable analogs (e.g., guanosine 5'-o-(3-thiotriphosphate) or GTPγS) may cause a two- to four-fold enhancement in the rate of $O_2^-$ generation by these systems (Gabig, et al., *J. Biol. Chem.* 262: 1685–1690 (1987); Seifert, et al., *FEBS Lett.* 205: 161–165 (1986)). More recently, we have demonstrated that there is an absolute requirement for GTP (or GTPγS) in the cell-free system (Uhlinger, et al., *J. Biol. Chem.* 266: 20990–20997 (1991); Peveri, et al., *PNAS USA* 89: 2494–2498 (1992)). Moreover, the NADPH oxidase activity of differentiated HL-60 cells is dependent upon prenylation of a cytosolic component (Bokoch and Prossnitz, *J. Clin. Invest.* 89: 402–408 (1992)). Taken together, this evidence is strongly indicative of a role for a GTP-binding protein in NADPH oxidase activation.

Two very closely related members of the Rho family of Ras-like LMWGs have recently been implicated in the regulation of NADPH oxidase. We purified Rac2 from human neutrophil cytosol on the basis of its ability both to bind GTPγS and stimulate $O_2^-$ generation in the presence of a suboptimal amount of neutrophil cytosol (Knaus, et al., *Science* 254: 1512–1515 (1991); Knaus, et al., *J. Biol. Chem.* 267: 23575–23582 (1992)). In similar experiments using guinea pig peritoneal macrophages, Rac1 was purified in an oxidase-enhancing complex (termed δ1) with Rho GDP dissociation inhibitor (RhoGDI). (See, e.g., Abo, et al., *Nature* 353: 668–670 (1991).) Subsequently, Mizuno, et al., *J. Biol. Chem.* 267: 10215–10218 (1992) also purified Rac2 from differentiated HL-60 cells, a human myeloid cell line, and confirmed that it enhances NADPH oxidase activity in a cell-free assay. A different approach was taken by Dorseuil and colleagues (*J. Biol. Chem.* 267: 20540–20542 (1992)), who used Epstein-Barr virus-transformed B lymphocytes that produce $O_2^-$ by an NADPH oxidase system similar (and perhaps identical) to the one in phagocytic cells. They showed that rac antisense (but not sense) oligonucleotides decreased the Rac protein content of the cells and inhibited $O_2^-$ generation in a dose-dependent manner, thus confirming the physiological role of Rac proteins in the regulation of NADPH oxidase activity. Rac1 and Rac2 are 92% identical and both undergo post-translational modification by the addition of a 20-carbon geranylgeranyl group to the cysteine of the carboxy-terminal CAAX box (Kinsella, et al., *J. Biol. Chem.* 266: 9786–9794 (1991)). Rac1 is expressed in a wide variety of cell types, whereas Rac2 is apparently restricted to cells of myeloid and lymphoid origin (Didsbury, et al., *J. Biol. Chem.* 264: 16378–16382 (1989); Reibel, et al., *Biochem. Biophys. Res. Commun.* 175: 451–458 (1991)).

SUMMARY OF THE INVENTION

The present invention contemplates methods of inhibiting the enzyme systems involved in the oxidative burst of phagocytic cells, as well as various peptides, compounds and compositions that are useful in such applications. In particular, the invention contemplates methods of disrupting or inhibiting the production of toxic oxygen products by phagocytic cells (e.g., neutrophils, macrophages), as well as compounds and compositions useful therefor. The present invention also contemplates the regulation of enzyme systems involved in the oxidative burst, for example, NADPH oxidase activity.

Another aspect of the present invention relates to a method for directly inhibiting activation of the specific enzyme system(s) involved in the oxidative burst of phagocytic cells, which involves administration of an effective amount of peptides according to the present invention which are capable of blocking superoxide production in phagocytic cells. The invention also relates to methods for preventing or decreasing tissue damage associated with phagocytic oxidative burst, which involves administration of the presently disclosed peptides as described above. Types of damage which may be prevented or remedied by compounds and compositions of the present invention include, for example, autoimmune disorders, myocardial infarction, gout, adult respiratory distress syndrome (ARDS), asthma, and various dermatological disorders.

One likely mechanism of action is the direct inhibition of activation of the specific enzymes/proteins involved in the oxidative burst of phagocytic cells, by binding to critical components of this system within phagocytic cells. Another viable mechanism of action involves competition for binding sites. It is thus believed that the peptide analogs and derivatives as disclosed herein will act only on phagocytic cells and will specifically decrease production of toxic oxygen products by these cells with a minimum of effect upon other cell types, tissues, and organ systems. It is not contemplated that the invention should be limited by a particular theory of action, however.

Therefore, in one embodiment, the present invention contemplates an optionally substituted, non-toxic peptide not more than 40 amino acids in length, wherein said peptide is capable of inhibiting superoxide production in phagocytic cells. In other embodiments, the peptide is about 3 to about 100 amino acids in length, preferably about 6 to about 40 amino acids in length, more preferably about 6 to about 30 amino acids in length, or about 6 to about 20 amino acids in length. In other variations, peptides of the present invention may be incorporated into liposomes, conjugated to targeting agents, or formulated into useful compositions.

Other useful polypeptides according to the present invention include proteins and peptides exhibiting GAP activity. Peptides homologous to at least a portion of, or derived from, p190-GAP or CDC42Hs-GAP are particularly preferred.

In one variation, the peptide is derived from a low molecular weight GTP binding protein (LMWG); in various alternative embodiments, the peptide is selected from the group consisting of ARF, ARF 26, ARF 27, ARF 28, Rac1, Rac2, Rap1A, Rap1B, and Rab3. In various embodiments, the peptide is selected from the group of amino acid residue sequences represented by the formulae: GNIFANLFKGLF-GKKE (SEQ ID NO 7), GLTISSLFSRLFGKKQ (SEQ ID NO 8), TISSLFSRLFGKKQ (SEQ ID NO 9), SSLFSRLF-GKKQ (SEQ ID NO 10), CPPPVKKRKRK (SEQ ID NO 11), CPQPTRQQKRA (SEQ ID NO 12), PGKARKKSS (SEQ ID NO 13), EKKKPKKKS (SEQ ID NO 14), and VSALGIDFKVKTTYRN (SEQ ID NO 15). In yet another embodiment, the peptide is derived from the carboxyl-terminal domain of a LMWG, or from the hypervariable region of a LMWG. In another variation, the peptides of the present invention may be used synergistically with antibodies directed against the same COOH-terminal site.

In another embodiment, the peptide comprises mastoparan or a derivative thereof. In alternative embodiments, the mastoparan-derived peptide is selected from the group of amino acid residue sequences represented by the formulae: INLKALAALAKKIL-NH$_2$ (SEQ ID NO 1), INLKALAALAKALL-NH$_2$ (SEQ ID NO 2), LKALAALAKKIL-NH$_2$ (SEQ ID NO 3), INWKGIAAMAKKLL-NH$_2$ (SEQ ID NO 4), and VDWKKIGQHILSVL-NH$_2$ (SEQ ID NO 5). In another variation, the present invention contemplates the use of mastoparan and mastoparan-like substances or peptides to stimulate or inhibit GDP/GTP exchange on LMWG. Another embodiment contemplates the use of mastoparan and mastoparan analogs to stimulate or inhibit GDP/GTP exchange on Rac and Rap polypeptides or proteins.

In an alternative embodiment, the peptide comprises ICS4 or a derivative thereof. An ICS4- derived peptide preferably comprises the amino acid residue sequence represented by the formula GLAQKLLEALQKALLA (SEQ ID NO 6).

In an alternative embodiment, an optionally substituted, non-toxic peptide capable of inhibiting superoxide production in phagocytic cells is selected from the group represented by the formula: GXXXXLFXXLFGKKX (SEQ ID NO 21), wherein X in each occurrence is independently selected from the group of amino acids consisting of G, S, T, C, N, Q, D, E, and H.

In yet another variation, an optionally substituted, non-toxic peptide capable of inhibiting superoxide production in phagocytic cells is selected from the group represented by the formula: [P'(X)$_a$(Z)$_a$], wherein P' represents a polar amino acid; X represents an amino acid selected from the group consisting of G, S, T, C, N, Q, D, E, and H; Z represents an amino acid selected from the group consisting of K and R; and a is 1 to 6. Alternatively, a preferred peptide according to the present invention is selected from the group represented by the formula: [G(X)$_a$(Z)$_a$], wherein X represents a hydrophobic amino acid selected from the group consisting of A, V, L, I, P, F, W, and M; Z represents an amino acid selected from the group consisting of K and R; and wherein a is 1 to 6.

Preferred peptides of the present invention may also be constructed to include a penetration-enhancing moiety attached to the peptide sequence, wherein the moiety comprises a hydrophobic group, an amphipathic group, or a cleavable ester group. In other variations, peptides as disclosed herein may be admixed with a penetration-enhancing agent to form an efficacious therapeutic composition. Other embodiments include the incorporation of preferred peptides or compositions into liposomes, or the attachment of preferred peptides to other molecules capable of targeting specific cells and/or delivering peptides across cell membranes. It should also be understood that various combinations of all the preceding elements may also describe efficacious peptides according to the present invention.

The present invention also contemplates a variety of useful compositions. For example, a preferred composition capable of inhibiting inflammation in animals comprises an optionally substituted, non-toxic peptide not more than 40 amino acids in length, wherein said peptide is capable of inhibiting superoxide production in phagocytic cells, in a pharmaceutically acceptable carrier or excipient. In a preferred embodiment, the animal is a human. Alternatively, preferred compositions according to the present invention may include any of the peptides described hereinabove—for example, and without limitation, LMWG peptides, GAPs, and mastoparan, to name but a few.

In another variation, the peptide is formulated to include a penetration-enhancing moiety, wherein the moiety comprises a hydrophobic group, an amphipathic group, or a clearable ester group. In another variation, the composition further comprises a penetration-enhancing agent. Further, any of the within-disclosed and contemplated compositions may be incorporated into liposomes. It will also be appreciated that various combinations of all the preceding elements may also describe a number of efficacious compositions according to the present invention.

The present invention also contemplates a method of inhibiting inflammation in an individual in need of treatment, comprising the administration of an effective amount of an NADPH oxidase inhibitor. In one variation, the inhibitor comprises a polypeptide or protein exhibiting GAP activity; in alternative embodiments, the polypeptide or protein is selected from the group consisting of p190 GAP, CDC42Hs GAP, and active polypeptide derivatives thereof.

In another embodiment, the NADPH oxidase inhibitor used according to the disclosed method comprises an optionally substituted, non-toxic peptide not more than 40 amino acids in length, wherein said peptide is capable of inhibiting superoxide production in phagocytic cells. As before, the polypeptide or peptide may be about 3 to about 100 amino acids in length, preferably about 6 to about 40 amino acids in length, more preferably about 6 to about 30 amino acids in length, or about 6 to about 20 amino acids in length.

In one alternative embodiment, the peptide is derived from a low molecular weight GTP binding protein (LMWG); in other alternative embodiments, the peptide is selected from the group of amino acid residue sequences represented by the formulae: GNIFANLFKGLFGKKE (SEQ ID NO 7), GLTISSLFSRLFGKKQ (SEQ ID NO 8), TISSLFSRLFGKKQ (SEQ ID NO 9), SSLFSRLFGKKQ (SEQ ID NO 10), CPPPVKKRKRK (SEQ ID NO 11), CPQPTRQQKRA (SEQ ID NO 12), PGKARKKSS (SEQ ID NO 13), EKKKPKKKS (SEQ ID NO 14), and VSALGIDFKVKTIYRN (SEQ ID NO 15).

The invention further contemplates that the NADPH oxidase inhibitor used according to the disclosed methods comprises ICS4, mastoparan or derivatives thereof. In various alternative embodiments, the peptide is selected from the group of amino acid residue sequences represented by the formulae: INLKALAALAKKIL-NH$_2$ (SEQ ID NO 1), INLKALAALAKALL-NH$_2$ (SEQ ID NO 2), LKALAALAKKIL-NH$_2$ (SEQ ID NO 3), INWKGIAAMAKKLL-NH$_2$ (SEQ ID NO 4), VDWKKIGQHILSVL-NH$_2$ (SEQ ID NO 5), and GLAQKLLEALQKALLA (SEQ ID NO 6).

ICS4 and ARF peptides are now shown to be capable of inhibiting O$_2^-$ production in the within-described assays. Their O$_2^-$-inhibiting activity may be related to the fact that these peptides possess a two- or three-dimensional structure similar to that of the active Rac peptides. However, they are not derived from Rac themselves which suggests that it is possible to design effective peptides once the structural basis for inhibitory actions of the Rac peptides is better understood. This should not, however, be construed to imply that the invention is limited to a particular theory of operation.

Inhibitory peptides other than those derived from Rac proteins and polypeptides are also expected to be useful according to the present invention. For example, peptides comprising amino acid residue sequences duplicating or mimicking sites on regulatory molecules or oxidase components which are capable of interacting with Rac proteins or peptides, and which may be useful as inhibitors of Rac-oxidase component interactions (or Rac-regulatory protein interactions), are also contemplated by the present invention. For example, an inhibitor may comprise a chimerin, Bcr protein, Abr protein, or a polypeptide derivative thereof. In other embodiments, the NADPH oxidase inhibitor comprises an optionally substituted, non-toxic peptide capable of inhibiting superoxide production in phagocytic cells. In short, peptides derived from—or homologous to—Rac proteins, oxidase components, or other regulatory molecules may be useful inhibitors of oxidative burst.

Alternatively, a method according to the present invention may utilize a peptide selected from the group represented by the formula: GXXXXLFXXLFGKKX (SEQ ID NO 21), wherein X in each occurrence is independently selected from the group of amino acids consisting of G, S, T, C, N, Q, D, E, and H, or may utilize a peptide selected from the group represented by the formula: [P'(X)$_a$(Z)$_a$], wherein P' represents a polar amino acid; X represents an amino acid selected from the group consisting of G, S, T, C, N, Q, D, E, and H; Z represents an amino acid selected from the group consisting of K and R; and a is 1 to 6.

Peptides selected from the group represented by the formula: [G(X)$_a$(Z)$_a$], wherein X represents a hydrophobic amino acid selected from the group consisting of A, V, L, I, P, F, W, and M; Z represents an amino acid selected from the group consisting of K and R; and wherein a is 1 to 6, may also be useful according to the within-disclosed methods.

Another aspect of the invention relates to a method for directly inhibiting activation of the specific enzyme system involved in the oxidative burst of phagocytic cells, and more preferably, human phagocytic cells. This method involves administration of an effective amount of optionally substituted peptide derivatives as disclosed herein. A further aspect relates to methods for preventing or decreasing the tissue damage associated with phagocyte oxidative burst which involves administration of an optionally substituted peptide derivative as described herein. The invention relates specifically to a method of preventing or decreasing symptoms such as gout, autoimmune disorders, myocardial infarction, adult respiratory distress syndrome (ARDS), asthma, and various dermatological disorders, which comprises the administration of an effective amount of a peptide derivative to a patient in need of such treatment.

The present invention also contemplates medicaments, and methods of making same, many of which methods are well known in pharmaceutical practice. For example, the peptides and derivatives of the present invention can be formulated into various forms for administration to mucous membranes, into intra-articular areas, intraperitoneally, intravascularly, topically, subcutaneously, and via suppository. Such medicaments may be formulated together with suitable carriers, excipients, binders, fillers, and the like into dosage forms, with each form comprising a fraction or a multiple of the daily dose required in order to achieve the desired result of treatment.

It will also be appreciated that various combinations of the preceding elements may be made to describe other efficacious peptides, compositions, and methods according to the present invention.

Finally, it is contemplated that the polypeptides, compositions and methods of the present invention may also be useful in veterinary applications, as well as in the treatment of humans.

BRIEF DESCRIPTION OF THE DRAWINGS

FIG. 9 illustrates a comparison of the effects of adding p190 GAP before and after initiation of NADPH oxidase activity. Time (in minutes; horizontal axis) is plotted against absorbance at 550 nm (vertical axis). Reaction mixtures contained $4 \times 10^5$ cell eq membranes and $1.8 \times 10^6$ cell eq of normal cytosol. Recombinant p190 GAP was added to reaction mixtures to give a final concentration of 350 nM either one minute before (closed, upright triangles) or 1.7 or 5 minutes after (closed, inverted triangles) the initiation of the reaction at 0 minutes with SDS (110 μM). In control reactions, buffer (open squares) or diphenylene iodonium (DPI, final concentration 1 μM, open circles) was added to ongoing reactions 1.7 (not shown for DPI) or 5 minutes after initiation.

DETAILED DESCRIPTION OF THE INVENTION

Figure 1:
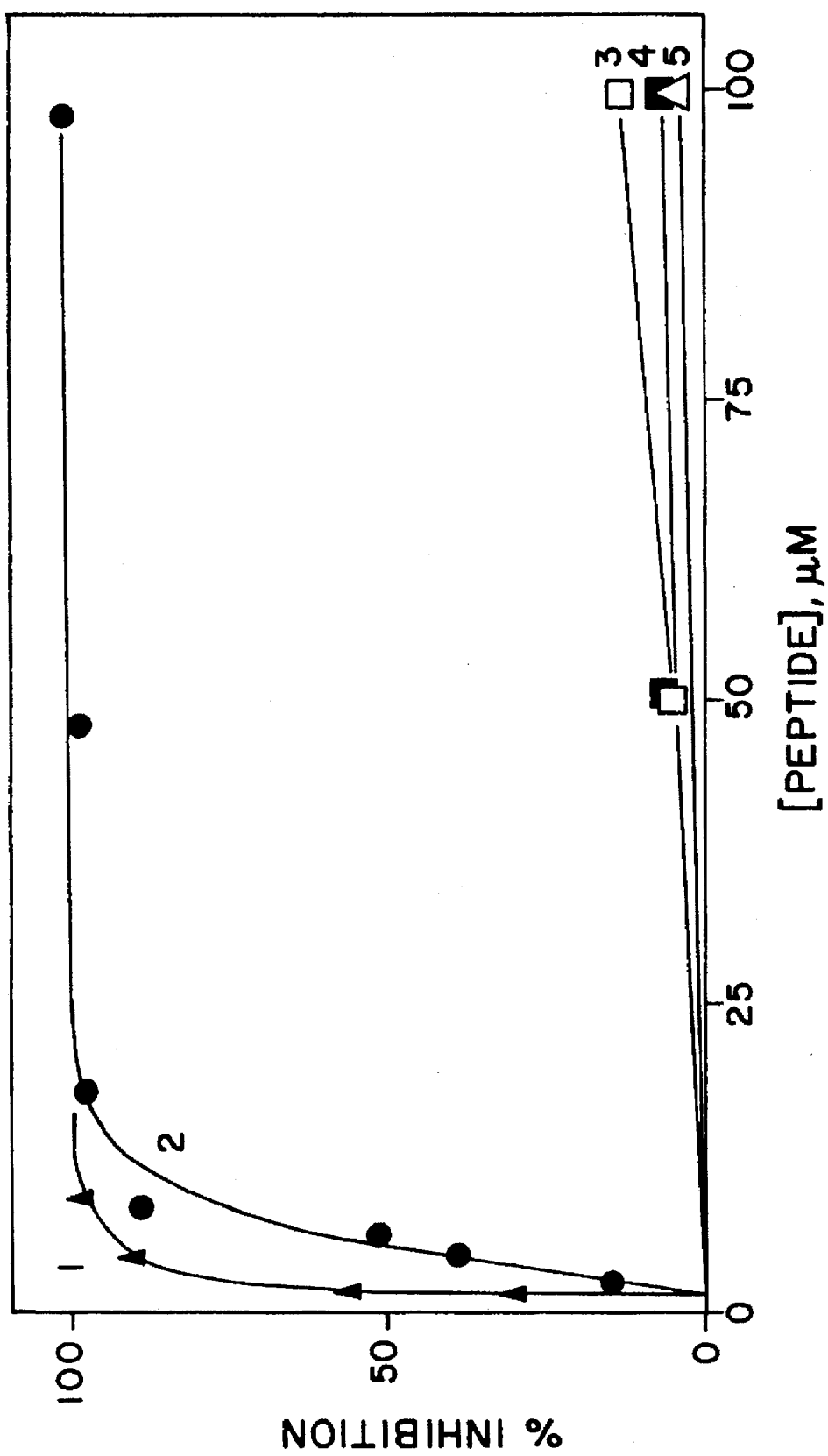
FIG. 1 illustrates inhibition of NADPH oxidase activity by various peptides in dose/response conditions. Percent inhibition is plotted against concentration of peptide in μM. Closed triangles (1) represent mastoparan; closed circles (2) represent Rac1 COOH-terminal peptide aa178–188; open squares (3) represent CDC42 COOH-terminal peptide; closed squares (4) represent Gi#2 control; and open triangles (5) represent Rac1 COOH-terminal peptide aa161–172.

It is now possible to inhibit the activation of NADPH oxidase and other enzyme systems involved in the oxidative burst of phagocytic cells via use of molecules derived from or homologous to GTP-binding proteins, particularly low molecular weight GTP-binding proteins (LMWG), including analogs and peptides derived therefrom. It is anticipated that molecules which specifically inhibit or otherwise regulate GDP/GTP exchange are also useful in this regard. Examples of useful molecules include mastoparan, mastoparan analogs, low molecular weight GTP-binding proteins (LMWG), and LMWG analogs, including optionally substituted peptide derivatives of LMWGs such as Rac1, Rac2, Rap1A, Rap1B, Rab3, and ARF. Examples of preferred derivatives include ICS4 (derived from Rab3), and peptides identified herein, including SEQ ID NOS 1–21.

I. Definitions

Amino Acid:

All amino acid residues identified herein are in the natural L-configuration. In keeping with standard polypeptide nomenclature, *J. Biol. Chem.* 243: 3557–59, (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-Leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues in the polypeptide chain.

Correspond in its various grammatical forms is used herein in relation to polypeptide sequences to mean the polypeptide sequence described plus or minus up to about three amino acid residues at either or both of the amino- and carboxy-termini and containing only conservative substitutions in particular amino acid residues along the polypeptide sequence.

p190 and p190 GAP are terms used interchangeably herein to designate a phosphoprotein with Rac GTPase activating ability.

Protein, polypeptide and peptide: protein, polypeptide and peptide are terms used herein to designate a series of amino acid residues connected one to the other by peptide bonds between the alpha-amino and carboxy groups of adjacent residues. In general, peptide and polypeptide are used interchangeably and refer to a series of fewer than about 100 amino acid residues connected one to the other, while protein is a term used herein to designate a series of greater than about 100 amino acid residues connected one to the other as in a polypeptide.

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous and are included within the scope of peptides, polypeptides or proteins defined by the terms "LMWG", "Rac", "Rap", and "mastoparan". Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Antibody in its various grammatical forms is used herein to refer to immunoglobulin molecules and immunologically active portions of immunoglobulin molecules, i.e., molecules that contain an antibody combining site or paratope. Illustrative antibody molecules include intact immunoglobulin molecules, substantially intact immunoglobulin molecules, and those portions of an immunoglobulin molecule that contain the paratope, including those portions known in the art as Fab, Fab', F(ab')$_2$ and F(v).

Antibody combining site refers to that structural portion of an antibody molecule comprised of a heavy and light chain variable and hypervariable regions that specifically binds (immunoreacts with) antigen.

The word antigen has been used historically to designate an entity that is bound by an antibody, and also to designate the entity that induces the production of the antibody. More current usage limits the meaning of antigen to that entity bound by an antibody, while the word immunogen is used for the entity that induces antibody production. In some instances, the antigen and immunogen are the same entity as where a synthetic polypeptide is utilized to induce production of antibodies that bind to the polypeptide.

Antigenic determinant refers to the actual structural portion of the antigen that is immunologically bound by an antibody combining site. The term is also used interchangeably with epitope.

Immunoreact in its various forms is used herein to refer to binding between an antigenic determinant-containing molecule and a molecule containing an antibody combining site such as a whole antibody molecule or a portion thereof.

Mastoparan, mastoparan derivatives, mastoparan analogs and their grammatical variations, as used herein, include the peptides identified herein as SEQ ID NOS 1–5, their derivatives, and analogs thereof, with and without a terminal amino (NH$_2$) group on the COOH-terminal end of the polypeptide.

Pharmaceutically acceptable, physiologically tolerable and their grammatical variations, as they refer to compositions, carriers, diluents and reagents, are used interchangeably and represent that the materials are capable of administration to or upon a mammal without the production of untoward physiological effects such as nausea, dizziness, gastric upset and the like.

Unit dose when used in reference to a therapeutic composition of the present invention refers to physically discrete units (U) suitable as unitary dosages for humans, each unit containing a predetermined quantity of active material calculated to produce the desired therapeutic effect in association with the required diluent, i.e., carrier, or vehicle.

II. Detailed Description

A. Polypeptides

A polypeptide of the present invention is at least about 6, and preferably not more than about 100, amino acids in length. Other preferred polypeptides are about 6 to about 40, and more preferably no more than about 25 to 30, amino acid residues in length. Useful polypeptides according to the present invention may also be about 6 to about 20 amino acids in length. In all instances, polypeptides of the present invention are capable of inhibiting oxidase activity or are capable of displaying GAP activity. Preferred polypeptides of the present invention are tolerant of various modifications (e.g., insertions, substitutions, and deletions), to the extent that such modifications do not destroy a particular peptide's ability to inhibit oxidase activity or to display GAP activity.

A polypeptide of the present invention may also be characterized as having an amino acid residue sequence homologous to or derived from the functional region of a larger polypeptide or protein displaying GAP activity or oxidase inhibitory activity. For example, a peptide according to the present invention may be homologous to the Rac2-COOH terminal region, as discussed further in Section II.B. below.

A polypeptide according to the present invention may include any analog, fragment or chemical derivative of a polypeptide whose amino acid residue sequence is shown herein so long as the polypeptide is capable of inhibiting the activation of oxidative enzyme systems, e.g., NADPH oxidase systems, in a manner corresponding to that of LMWG peptides or proteins, or peptides and proteins exhibiting GAP activity. Therefore, a polypeptide of the present invention can be subject to various changes, substitutions, insertions, and deletions where such changes provide for certain advantages in its use. (See Section II.B. below.)

The term "fragment" refers to any subject polypeptide having an amino acid residue sequence shorter than that of a polypeptide whose amino acid residue sequence is shown herein.

Preferred peptides according to the present invention include peptides which are capable of GTP/GDP regulatory activity. In particular, GTP-binding proteins and their analogs are ideal candidates and sources of useful peptides.

One group of useful peptides is derived from the Ras superfamily. There are a number of common features among the Ras superfamily of GTP-binding proteins. These common features include structural similarities; for example, all Ras-related proteins have a conserved guanine nucleotide binding and hydrolysis domain. (See, e.g., Valencia, et al., *Biochemistry* 30: 4637–4648 (1991).) Second, all Ras-related proteins undergo post-translational processing by isoprenylation (C20 or C15) and/or palmitylation. In addition, many of the Ras-related proteins are truncated and/or carboxymethylated. Finally, the C-terminal CAAX motif is most common.

The post-translationally modified C terminus of the Ras-related proteins is also known to be important for the membrane association of those proteins, as well as for their biological activity. There are also a variety of extrinsic regulatory proteins including GAP (GTPase activating protein), GDI (GDP dissociation inhibitor) and GDS (GDP/GTP dissociation stimulator). The binding of GDI and/or GDS requires C terminal processing and can regulate whether the GTP binding protein is membrane associated or cytosolic.

GAPs, GDSs, and GDIs are capable of modulating the GTP/GDP state of Rac (Bokoch and Der, *FASEB J.* 7: 750–759 (1993)). GAPs stimulate GTP hydrolysis, while GDSs promote the exchange of GTP for GDP. GDIs inhibit GDP dissociation from Rac, but GDIs are also able to inhibit the intrinsic GTP hydrolytic activity of Rac, as well as that stimulated by GAPs. (See also Chuang, et al., *J. Biol. Chem.* 268: 775–778 (1993).)

The presence of [Rho]GDI in human neutrophils and other phagocytes is well established, and a Rac GDS activity has also been detected. (See, e.g., Knaus, et al., *J. Biol. Chem.* 267: 23575–223582 (1992); Kwong, et al., *Biochemistry* 32: 5711–5717 (1993); Abo, et al., *Nature* 353: 668–670 (1991); and Heyworth, et al., *Mol. Biol. Cell* 4: 261–269 (1993).) ([Rho]GDI refers to a GDI originally described to be active on Rho (Ueda, et al., *J. Biol. Chem.* 265: 9373–9380 (1990)) but which now is known to be active on other members of the Rho family.)

The addition of exogenous [Rho]GDI and smgGDS to cell-free oxidase systems has demonstrated that these proteins can regulate NADPH oxidase activity, probably through effects on Rac to prevent or stimulate GTP/GDP exchange, respectively. (See Mizuno, et al., *J. Biol. Chem.* 267: 10215–10218 (1992).) Regulatory roles for Rac GAPs in the oxidase system have not been described. Since there is evidence that GAPs might act as downstream effectors as well as negative regulators, at least in certain systems, the activities of GAP proteins remain to be determined for each particular protein.

A variety of molecules with GAP activity for Rac have been described. (See Bokoch and Der, Id. (1992); Hall, et al., *Cell* 69: 389–391 (1992).) Among these are the p190 protein, which tightly associates with p120 Ras GAP upon activation of growth factor receptor and transforming tyrosine kinases (Ellis, et al., *Nature* 343: 377–381 (1990); Settleman, et al., *Cell* 69: 539–549 (1992); Settleman, et al., *Nature* 359: 153–154 (1992)) and a distinct GAP, termed CDC42 GAP, that has activity for the Rac-related GTP-binding protein CDC42 (Hart, et al., *J. Biol. Chem.* 266: 20840–20848 (1991)). This GAP appears to be identical to a previously identified Rho GAP (Garrett, et al., *J. Biol. Chem.* 264: 10–13 (1989)). Although Rac GAP activity has been detected in human neutrophils (Bokoch, G. M., unpublished observation), the proteins that mediate this activity in human phagocytes have not yet been identified.

It is demonstrated herein that p190 Rac GAP is present in human neutrophils and is able to inhibit NADPH oxidase activity in a cell-free $O_2^-$ generating system. This inhibition appears to be the result of modulation of the GTP state of Rac and can be reversed by the addition of pre-activated forms of Rac. The use of p190 Rac GAP to investigate Rac in the active NADPH oxidase complex is also demonstrated herein, as is the usefulness of GAPs (and derivatives and analogs thereof) as NADPH oxidase inhibitors. Our findings also suggest that other proteins having activity similar to CDC42Hs would be useful inhibitors; these proteins include Bcr protein, Abr protein, and chimerins.

Rac1, Rac2, and related proteins are also the source of useful peptides. Rac1 and Rac2 are very closely-related members of the Rho family of Ras-like low molecular weight GTP-binding proteins which are implicated in the regulation of NADPH oxidase. Rac2 may be purified from human neutrophil cytosol on the basis of its ability both to bind GTPγS and to stimulate $O_2^-$ generation in the presence of a suboptimal amount of neutrophil cytosol. (See, e.g., Knaus, et al., *Science* 254: 1512–1515 (1991); Knaus, et al., *J. Biol. Chem.* 267: 23575–23582 (1992).) In similar experiments using guinea pig peritoneal macrophages, Rac1 was purified in an oxidase-enhancing complex (termed rho1) with Rho GDP dissociation inhibitor (RhoGDI). (See, e.g., Abo, et al., *Nature* 353: 668–670 (1991).)

Rac1 and Rac2 are 92% identical and both undergo posttranslational modification by the addition of a 20-carbon geranylgeranyl group to the cysteine of the carboxy-terminal CAAX box. Rac1 is expressed in a wide variety of cell types, whereas Rac2 is apparently restricted to cells of myeloid and lymphoid origin. (See, e.g., Didsbury, et al., *J. Biol. Chem.* 264: 16378–16382 (1989); Reibel, et al., *Biochem. Biophys. Res. Commun.* 175: 451–458 (1991).)

The importance of the C terminal region in oxidase regulation/activity is indicated by the following. First, the oxidase in the cells is inhibited by drugs which block isoprenylation. Second, inhibition by anti-peptide antibodies to Rac2 amino acids 178–188 (C terminus) is noted. Finally, inhibition by Rac1 and Rac2 C-terminal peptides is significant (see data described hereinbelow).

The within-described research has allowed us to identify a key protein or proteins involved in NADPH oxidase activation in phagocytic cells. These proteins, including Rac2 and Rap1A —and perhaps Rac1 as well—regulate the activity of the NADPH oxidase in neutrophils and other cells, acting at key regulatory step in the activation pathway. The ability of peptide(s) representing the COOH terminal portion of Rac2 (and Rap1A) to inhibit activation of the NADPH oxidase in a cell-free system is disclosed herein. Such peptides may provide a means to specifically inhibit the activation of the phagocyte NADPH oxidase, since Rac2 is found only in cells of myeloid origin. In addition, small molecular weight inhibitors other than peptides might be identified. The concept that the COOH terminal portion of these proteins is important for key regulatory interactions involved in NADPH oxidase activity is also disclosed herein. The use of such potentially specific inhibitors would provide a means to inhibit inappropriate phagocyte generation of oxygen radicals and alleviate inflammatory processes resulting from such activity.

A rapidly growing superfamily of LMWGs is presently being identified via protein purification, immunological, and recombinant technologies (Der, in *Oncogenes*, Benz & Liu (eds), Kluweer Academic, Boston, Mass., 1989, pp. 73–119; Hall, *Science* 249: 635–640 (1990); Santos, et al., *FASEB J.* 3: 2151–2163 (1989); and Downward, *Trends Biochem. Sci.* 15: 469–472 (1990)). This superfamily currently consists of approximately 50 monomeric proteins in the size range of about 18–28 kilodaltons (kDa). Based on primary sequence, these proteins have been subdivided into three major families.

The ras oncogene products were the original LMWGs to be discovered and are the most extensively studied. The 21 kDa Ha-, Ki-, and N-Ras are believed to be involved in growth factor-mediated signal transduction, either by modulating known second messenger systems or by acting through a novel pathway or pathways. (See, e.g., Kaplan, et al., *Cell* 61: 125–133 (1990); Cantley, et al., *Cell* 64: 281–302 (1991); Quilliam, et al., *Second Messengers Protein Phosphorylation* 13: (1990); Gibbs, et al., *J. Biol. Chem.* 265: 20437–20442 (1990); Smith, et al., *Nature* 320: 540–543 (1986); Yatani, et al., *Cell* 60: 769–776 (1990); and Okamoto, et al., *J. Biol. Chem.* 266: 1085–1091 (1991).) The Ras family of LMWGs consists of an additional seven proteins that have approximately 50% homology with Ras. These include R-Ras (Lowe, et al., *Mol. Cell. Biol.* 7: 2845–2856 (1987)), Ral A and B (Chardin, et al., *NAR* 17: 4380 (1989)), and the Rap subfamily (Pizon, et al., *Oncogene* 3: 201–4 (1988); Pizon, et al., *NAR* 16: 7719 (1988); Ohmstede, *PNAS USA* 87: 6527–6531 (1990)). The functions of the former are unknown, while the Rap proteins are believed to act antagonistically to Ras action and to phagocytic function(s). There are four Raps, including Rap1A and Rap1B, which are 95% homologous, and Rap2 and Rap2B, which share a 90% homology with each other and are about 70% homologous with Rap1A. Rap1A was independently cloned by several groups (Pizon, et al., Id.; Quilliam, et al., *Mol. Cell. Biol.* 10: 2901–2908 (1990); and is also known as Krev-1 (Kitayama, *Cell* 56: 77–84 (1989)) and smg p21 (Kawata, et al., *J. Biol. Chem.* 263: 19865–18971 (1988)).

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

B. Peptide Analogs and Derivatives

The term "analog" includes any polypeptide having an amino acid residue sequence substantially identical to a sequence specifically shown herein in which one or more residues have been conservatively substituted with a functionally similar residue and which displays the ability to functionally mimic LMWG as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

"Conservative substitution" as used herein is meant to denote that one amino acid residue has been replaced by another, biologically or chemically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like. The term "conservative substitution" also includes the use of a substituted amino acid in place of an unsubstituted parent amino acid provided that such a polypeptide also displays the requisite binding activity. The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The peptide derivatives and analogs of the present invention include optionally-substituted peptides and polypeptide derivatives which block the production of superoxides and other toxic oxygen products in phagocytic cells. The sequence of the peptide derivatives or analogs may be linear or non-linear, albeit linear peptide derivatives or analogs represent a preferred embodiment. A peptide derivative or analog of the present invention is at least about 3, more preferably 6, and no more than about 100, preferably no more than about 40, and more preferably no more than about 25 to 30, amino acid residues in length.

It is also contemplated that addition of a certain class of chemical moieties selected from hydrophobic and amphipathic groups will enhance the penetration of the peptides, derivatives and analogs of the present invention into phagocytic cells. Addition of such moieties may also assist in the retention of such peptides, derivatives, and analogs within phagocytic cells.

Examples of such auxiliary groups and moieties include cleavable ester groups such as acetoxy-methylester, which has been successfully used to modify hydrophilic, ionic chemical substances which may then pass through the lipid barrier of the cell exterior and into the interior of living cells and tissues. (See, e.g., Grynkiewicz, et al., *J. Biol. Chem.* 260: 3440–3450 (1985), which is incorporated herein by reference.) When the peptides, derivatives, or analogs are to be used in warm-blooded animals, including humans, it is appreciated that the derivatization should not render the peptide derivatives toxic. Peptide derivatives with added chemical moieties as described above are considered pro-drugs for the active peptide derivatives or analogs.

Figure 2:
FIG. 2 illustrates that the activity of Rac1 peptide can be retained by a peptide as small as 6 amino acids in length. Percent inhibition is plotted against concentration in μM. Closed circles represent Rac1 11-mer peptide; closed squares represent Rac1 9-mer peptide; closed triangles represent Rac1 6-mer peptide; open circles represent Rac2 11-mer peptide; and open squares represent Rac2 9-mer peptide.
Figure 3:
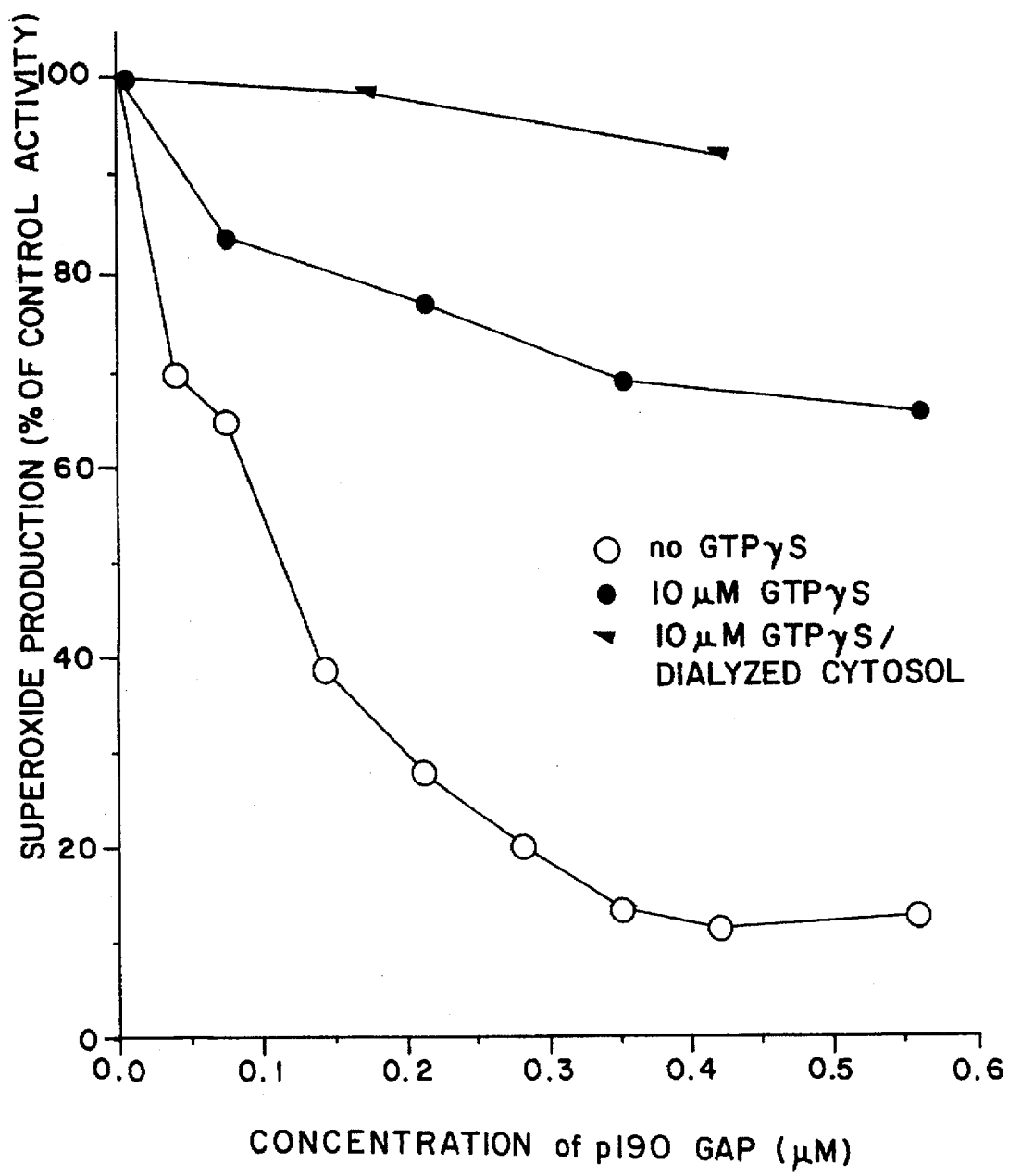
FIG. 3 illustrates the effect of p190 GAP on NADPH oxidase activity in the presence and absence of GTPγS. The concentration of p190 GAP (in μM; horizontal axis) is plotted against superoxide production (percent of control activity; vertical axis). Recombinant p190 GAP was added to reaction mixtures to give the final concentrations indicated, one minute prior to activation of $O_2^-$ production with SDS. Reaction mixtures contained $4 \times 10^5$ cell eq membranes and $1.8 \times 10^6$ cell eq of either normal cytosol (open circles, closed circles) or dialyzed cytosol (closed triangles). The final concentrations of endogenous GTP contributed by this amount of normal and dialyzed cytosol were 2.8 μM and <0.02 μM, respectively. Reactions were either performed at 2.8 μM GTP (open circles), or were supplemented with 10 μM GTPγS (closed circles, closed triangles). The control rate of $O_2^-$ production was 26.7±3.2 (S.D., n=4) nmol/min/$10^7$ cell eq membranes. Data shown are representative of at least two experiments.

Tables 1 and 2 hereinbelow list peptides assayed via $O_2^-$ activity tests and in oxidase assays, some of which are identified herein as useful according to the present invention. Results of the assays are discussed further below and are illustrated in FIGS. 1–3.

TABLE 1

| PEPTIDES USED FOR $O_2$ ACTIVITY TESTS | | |
|---|---|---|
| Derivative | Residue No. or Length | Sequence/(SEQ ID NO) |
| Rac1 | 178–188 | CPPPVKKRKRK (SEQ ID NO 11) |
| Rac1 | 161–172 | LTQRGLKTVFDE (SEQ ID NO 16) |

TABLE 1-continued

| PEPTIDES USED FOR $O_2$ ACTIVITY TESTS | | |
|---|---|---|
| Derivative | Residue No. or Length | Sequence/(SEQ ID NO) |
| Rac1 | 127–137 | EKLKEKKLTPI (SEQ ID NO 17) |
| Rac2 | 178–188 | CPQPTRQQKRA (SEQ ID NO 12) |
| Rap1b | 172–180 | PGKARKKSS (SEQ ID NO 13) |
| Rap1a | 172–180 | EKKKPKKKS (SEQ ID NO 14) |
| Mastoparan | 14 aa | INLKALAALAKKIL-NH$_2$ (SEQ ID NO 1) |
| Mastoparan 7 | 14 aa | INLKALAALAKALL-NH$_2$ (SEQ ID NO 2) |
| Mastoparan 3 | 12 aa | LKALAALAKKIL-NH$_2$ (SEQ ID NO 3) |
| Mastoparan Polistes | 14 aa | VDWKKIGQHILSVL-NH$_2$ (SEQ ID NO 5) |
| Mastoparan X | 14 aa | INWKGIAAMAKKLL-NH$_2$ (SEQ ID NO 4) |
| Rab3 | 16 aa | VSALGIDFKVKTIYRN (SEQ ID NO 15) |
| G$_i$ #2 | 12 aa | SKFEDLNKRKDT (SEQ ID NO 18) |
| G$_i$ #5 | 15 aa | MGCTVSAEDKAAAER (SEQ ID NO 19) |
| CDC42Hs | 167–188 | KNVFDEAILAALEPPEPKKSRR (SEQ ID NO 20) |
| ECG125 | | amphipathic helix |
| ECG163 | | disrupted helix |
| ARF | 16 aa | GNIFANLFKGLFGKKE (SEQ ID NO 7) |
| ARF26 | 16 aa | GLTISSLFSRLFGKKQ (SEQ ID NO 8) |
| ARF27 | 14 aa | TISSLFSRLFGKKQ (SEQ ID NO 9) |
| ARF28 | 12 aa | SSLFSRLFGKKQ (SEQ ID NO 10) |

TABLE 2

SEQUENCES OF MASTOPARAN AND RELATED PEPTIDES USED IN OXIDASE ASSAYS

| | |
|---|---|
| Rab3 | VSALGIDFKVKTIYRN |
| Mastoparan 7 | INLKALAALAKALL |
| Mastoparan | INLKALAALAKKIL |
| | ⋮ ⋮ \ * |
| ARF | GNIFANLFKGLFGKKE |
| | ⋮ ⋮ ⋮ |
| ICS4 | GLAQKLLEALQKALLA (SEQ ID NO 6) |
| | ⋮ ⋮ ⋮ |
| ECG125 | GELAQKLEQALQKLA (SEQ ID NO 22) |
| | ⋮ ⋮ ⋮ |
| ECG163 | GEHAQKHEQALQKLA (SEQ ID NO 23) |

*Bar (⋮) indicates helical repeat

C. Methods for Producing A Subject Polypeptide, Derivative, or Analog

A subject polypeptide, derivative or analog can be prepared using recombinant nucleic acid methodologies well known in the art. For instance, DNA sequences useful in producing a subject polypeptide are described in Paik et al., *PNAS USA* 82: 3445–3449, (1985); McLean et al., *J. Biol. Chem.* 259: 6498–6504, (1984); and Rall et al., *J. Biol. Chem.* 257: 4171–4178, (1982). A DNA segment coding for a polypeptide of this invention can be synthesized by chemical techniques, for example the phosphotriester method of Matteucci et al., *J. Am. Chem. Soc.* 103: 3185, (1981). The DNA segment can then be ligated into an expression vector, and a host transformed therewith can be used to produce the polypeptide. See, for example, *Current Protocols In Molecular Biology*, Ausubel et al., eds., John Wiley & Sons, New York, N.Y.; and U.S. Pat. No. 4,237,224 and No. 4,356,270, the disclosures of which are hereby incorporated by reference.

The recombinant expression vectors capable of expressing a subject polypeptide and methods of their use for producing a subject polypeptide are contemplated as part of the present invention.

A polypeptide of the present invention can be synthesized by any of the peptide synthetic techniques known to those skilled in the art. A summary of some of the techniques available can be found in J. Meinhofer, "Hormonal Proteins and Peptides" Vol. 2, pp. 46, Academic Press (New York) 1983, and U.S. Pat. No. 4,631,211, which description is incorporated herein by reference. When a polypeptide desired for use in the present invention is relatively short (less than about 40 amino acid residues in length) direct peptide synthetic techniques are generally favored, usually by employing a solid phase technique such as that initially described by Merrifield, in *J. Am. Chem. Soc.* 85: 2149–2154 (1963).

Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104–237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

Use of automated peptide synthesizers is also contemplated by the present invention. For example, the within-described peptides may be synthesized using an Applied Biosystems 430A Automated Synthesizer following the manufacturer's instructions. Synthesized peptides may then be cleaved from the resin and deblocked using hydrofluoric acid following standard procedures as described. After neutralization to pH 7 (e.g., with sodium hydroxide), the peptides may be dialyzed into ammonium carbonate buffer and then lyophilized. Sequences may then be confirmed via peptide composition analysis.

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

Another aspect of the present invention pertains to methods for producing subject polypeptides, analogs, or derivatives useful for inhibiting or preventing activation of NADPH oxidase and other enzyme systems involved in the oxidative burst of phagocytic cells which may be used in the diagnostic systems and methods of the present invention.

One such method entails initiating a culture comprising a nutrient medium containing host cells transformed with a recombinant DNA molecule of the present invention that is capable of expressing a gene encoding a subject peptide, such as a peptide corresponding or substantially homologous to a formula shown in Table 1 or 2. The culture is maintained for a time period sufficient for the transformed cells to express the subject polypeptide. The expressed polypeptide is then recovered from the culture. (While this method may be used to synthesize smaller polypeptides as described herein, it tends to be used more often for the expression of larger polypeptides and protein molecules.)

Methods for recovering an expressed polypeptide from a culture are well known in the art and include fractionation of the polypeptide-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoabsorption and the like can be performed using well known methods.

Peptides may also be synthesized using polymerase chain reaction (PCR) techniques. Using PCR, it is possible to synthesize useful polypeptide-encoding nucleotide sequences which may then be operatively linked to a vector and used to transform an appropriate cell and expressed therein.

Particularly preferred methods for producing large quantities of peptides and proteins such as those of the present invention rely on the use of preselected oligonucleotides as primers in a PCR to form PCR reaction products. If the DNA products are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among the preferred gene's plus (or coding) strands. To produce coding DNA homologs, first primers are therefore chosen to hybridize to (i.e. be complementary to) conserved regions within the gene(s) of choice.

Second primers become part of the coding (plus) strand and hybridize to a nucleotide sequence conserved among minus strands. To produce the coding DNA homologs, second primers are therefore chosen to hybridize with a conserved nucleotide sequence at the 5' end of the coding gene such as in that area coding for the leader or first framework region. It should be noted that in the amplification of the coding DNA homologs the conserved 5' nucleotide sequence of the second primer can be complementary to a sequence exogenously added using terminal deoxynucleotidyl transferase as described by Loh et al., *Science* 243: 217–220 (1989). One or both of the first and second primers can contain a nucleotide sequence defining an endonuclease recognition site (restriction site). The site can be heterologous to the gene being amplified and typically appears at or near the 5' end of the primer.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to produce a DNA molecule having cohesive termini that are non-complementary to each other and thus allow directional insertion into a vector.

In PCR, each primer works in combination with a second primer to amplify a target nucleic acid sequence. The choice of PCR primer pairs for use in PCR is governed by various considerations, as is known in the art. That is, the primers have a nucleotide sequence that is complementary to a sequence conserved in the gene of choice. The strategy used for cloning the selected genes will depend, as is well known in the art, on the type, complexity, and purity of the nucleic acids making up the various genes. Other factors include whether or not the genes are to be amplified and/or mutagenized.

Useful components of a PCR reaction are readily available. For example, *Thermus aquaticus* DNA polymerase I is described in U.S. Pat. No. 4,889,818. Similarly, useful inducing agents are described in Chamberlin et al., *The Enzymes*, ed. P. Boyer, PP. 87–108, Academic Press, New York (1982) and Joyce, et al., *Nuc. Acid Res.* 17: 711–722 (1989), to name two examples. Amplification systems based on transcription have also been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above. The newly synthesized strand and its complementary nucleic acid strand form a double-stranded molecule which can be used in the succeeding steps of the process.

After producing various polypeptide-encoding DNA homologs for one or a plurality of different genes or DNA segments, the DNA molecules are typically further amplified. PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers are also described in Nilsson, et al., *Cell* 58: 707 (1989), Ennis, et al., *PNAS USA* 87: 2833–7 (1990), and Zemmour, et al., *Immunogenetics* 33: 310–20 (1991), for example. It is usually preferred to design primers from comparison of 5' and 3' untranslated regions of known allelic forms, with selection of conserved sequences. Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

D. Production and Purification of Proteins Obtained Via Recombinant Means

Recombinant peptides or proteins may be prepared and purified essentially as follows. (Rac1 and Rac2 proteins are described herein as exemplary proteins.) Recombinant Rac2 was expressed in *E. coli* and purified according to the methods reported in Knaus, et al., *J. Biol. Chem.* 267: 23575–23582 (1992). The full-length cDNA encoding Rac1 was subcloned into the BamHi site on the expression vector pET3a (Novagen, Madison, Wis.). *E. coli* strain BL21-DE3 (Novagen, Madison, Wis.) was used as the host cell for the recombinant plasmid identified as pER1, and was grown in LB medium at 37° C. until an $OD_{600}$ (optical density reading at 600 nm) of 0.7–0.9 was reached. Isopropyl β-D-thiogalactopyranoside was added to a final concentration of 1 mM to induce protein expression. The cells were grown for an additional 2 hours at 37° C, harvested by centrifugation at 5000 g and 4° C. for 15 minutes, resuspended in 25 mM Tris-HCl (pH 8.0), 1 mM EDTA, 5 mM dithiothreitol, 5 mM $MgCl_2$ 0.5 mM phenylmethylsulfonyl fluoride, and incubated for 1 hour at 25° C. on this buffer, supplemented with lysozyme (0.5 mg/ml) and deoxyribonuclease I (10 µg/ml). The suspension was then subjected to two 10-second bursts of sonication at 4° C. and to one cycle of freezing and thawing. After centrifugation for 25 minutes at 15,000 g, the supernatant was dialyzed against equilibration buffer (25 mM Tris-HCl (pH 8.0), 1 mM EDTA, 5 mM $MgCl_2$, 5 mM dithiothreitol, 1 mM 2-mercaptoethanol, 1 mM phenylmethylsulfonyl fluoride) and applied to a MonoQ HR 5/5 column (pre-equilibrated with the same buffer) connected to an FPLC system (Pharmacia LKB, Piscataway, N.J.). The column was washed extensively with equilibration buffer and eluted at a flow rate of 0.5 ml/min with a 30 ml linear gradient of 0–300 mM NaCl, followed by a steeper 15 ml gradient of 300–1000 mM NaCl, both in the same buffer. The *E. coli* recombinant Rac1 eluted at 100–120 mM NaCl. This material was 70–80% pure as estimated by silver staining.

Recombinant proteins expressed in bacterial systems do not undergo the normal post-translational processing of the native protein, and may be referred to as unprocessed protein. This was confirmed by the inability of *E. coli*-expressed Rac1 and Rac2 to partition into the detergent phase upon Triton X-114 partitioning analysis (Bordier, *J. Biol. Chem.* 256: 1604–1607 (1991)). In order to produce forms of Rac1 and Rac2 that had undergone post-translational modification (referred to as processed protein), a baculovirus/insect cell expression system was also utilized. The full-length cDNAs encoding Rac1 and Rac2, each with an additional sequence coding or the N-terminal epitope tag Met-Glu-Glu-Glu-Glu-Tyr-Met-Pro-Met-Glu (SEQ ID NO 24), were subcloned into the baculovirus transfer vector pAc13 (a gift from Dr. Channing Der, University of North Carolina, Chapel Hill, N.C.) so as to place these genes under the control of the polyhedrin promoter. (Other comparable, useful vectors are available from Invitrogen, Inc., La Jolla, Calif., or from Dr. Max D. Summers, Texas Agricultural Experimental Station, Tex.) *Spodoptera frugiperda* host cells (Sf9) were cotransfected with the Rac-containing transfer vector and wild-type baculovirus (AcMNPV) DNA. (See, e.g., Summers and Smith, *Tex. Agric. Exp. Stn. Bull.* 1555: 1–57 (1987).) Recombinant viruses were identified using a standard plaque assay, and virus from a single plaque was amplified and used to infect Sf9 cells during log phase growth. Cells were harvested at 72 hours post-infection.

In order to purify the recombinant Rac, the baculovirus cell pellet was subjected to $N_2$ cavitation at 450 psi and 4° C. for 20 minutes in a buffer consisting of 100 mM KCl, 3 mM NaCl, 3.5 mM $MgCl_2$, 10 mM PIPES (pH 7.3; Sigma Chemical Co., St. Louis, Mo.), 1 mM phenylmethylsulfonyl fluoride, 100 kallikrein inhibitory units of aprotonin/ml, 1 µM leupeptin, 1 mM 2-mercaptoethanol and 0.2 mM dithiothreitol. The cavitated cells were collected into sufficient EGTA (Sigma) to give a final concentration of 1 mM and centrifuged at 1,000 g and 4° C. for 10 minutes to remove unbroken cells. The supernatant was centrifuged at 100,000 g for 35 minutes and the cytosol was removed from the pellet. The pellet (containing cell membranes) was washed once with a buffer containing 10 mM Tris-HCl (pH 8.0), 1 mM EDTA, 10 mM $MgCl_2$, 50 mM NaCl, 0.1 mM dithiothreitol, 1 mM phenylmethylsulfonyl fluoride, and 1 mM 2-mercaptoethanol, to insure removal of contaminating cytosol, solubilized in extraction buffer (25 mM Tris-HCl (pH 7.5), 1 mM EDTA, 5 mM $MgCl_2$, 0.1 mM dithiothreitol, 1 mM phenylmethylsulfonyl fluoride, and 0.9% cholate) for 4 hours on ice, and centrifuged at 100,000 g for 35 minutes. The supernatant was applied to a column of Protein G Sepharose 4 Fast Flow (Pharmacia LKB, Piscataway, N.J.) crosslinked with a monoclonal antibody to the peptide Glu-Glu-Glu-Glu-Tyr-Met-Pro-Met-Glu (SEQ ID NO 24 from position 2 to 10), previously pre-equilibrated with extraction buffer (Grussenmeyer, et al.1, PNAS USA 82: 7952–7954 (1985)). After application of the supernatant, the column was washed with 15 column volumes of extraction buffer followed by 10 column volumes of extraction buffer containing 100 mM NaCl. Bound protein was then eluted with a solution of peptide (Glu-Glu-Tyr-Met-Pro-Met-Glu) (SEQ ID NO 24 from position 4 to 10) in extraction buffer, at a concentration of 100 µg/ml. These methods produced highly pure preparations of Rac2 and Rac1, as shown by silver staining (data not shown). These proteins were shown to be isoprenylated by the incorporation of [$^3$H]mevalonic acid.

Recombinant full length Rap1a, H-Ras, and CDC42Hs were purified after expression in a baculovirus/Sf9 insect cell system, using previously reported methods (Quilliam, et al., Id. (1990); Hart, et al., J. Biol. Chem. 266: 20840–20848 (1991). Recombinant forms of the neutrophil NADPH oxidase cytosolic components, p47-phox and p67-phox, were expressed in a similar system using the full-length cDNA clones and purified to near-homogeneity, employing methods described by Uhlinger, et al., Biochem. Biophys. Res. Commun. 186: 509–516 (1992)).

Other useful methods of expressing polypeptides are disclosed in the art; see, e.g., Quilliam, et al., Mol. Cell. Biol. 10: 2901–2908 (1990), and Hart, et al., J. Biol. Chem. 266: 20840–20848 (1991).

E. Molecules Capable of Mimicking or Inhibiting GTP/GDP Regulatory Molecules

The present invention also contemplates the use of molecules capable of mimicking, inhibiting, or otherwise modifying the activity/effect of GTP/GDP regulatory molecules, thereby regulating the NADPH oxidase system of phagocytes. Examples of such useful molecules include mastoparan and mastoparan-like substances or peptides, which may be used to stimulate or inhibit GDP/GTP exchange on LMWG. Mastoparan and mastoparan analogs may also be used to stimulate GDP/GTP exchange on Rac and Rap polypeptides or proteins.

Mastoparan is a peptide of 14 amino acids in length which was originally derived from wasp venom. It has been suggested that it mimics a portion of the structure of receptors coupled to GTP binding proteins of the heterotrimene type (not LMWG) and thereby causes GDP/GTP exchange on these proteins. It is now shown that mastoparan and its analogs (including derivatives including or lacking an amino group at what is typically the carboxy-terminus of the polypeptide) also stimulate GDP/GTP exchange on the LMWG, including Rac and Rap1A. This effect may correlate with the ability of mastoparan to effectively inhibit NADPH oxidase activity in the cell-free system.

Other molecules such as GDP dissociation inhibitors (GDI) may also be used according to the present invention. For example, (Rho)GDI has now been reported to have a concentration-dependent effect on GTP hydrolysis by Rac1, parallelling its ability to inhibit GDP dissociation from the Rac protein (Chuang, et al., J. Biol. Chem. 268: 775–778 (1993)). Other examples include Bcr, the product of the rearranged gene found in Philadelphia chromosome-positive CMLs and several chronic CLLs, which may act as a GTP-ase activating protein (GAP) for Rac, as may the related brain protein n-chimerin. (See, e.g., Chuang, et al., J. Biol. Chem. 268: 775–778 (1993); and Diekmann, et al., Nature 351: 400–402 (1991).) Protein p190, which forms a complex with Ras-GAP subsequent to cell activation by growth factors or transforming tyrosine kinases, may also stimulate Rac GTP hydrolysis (Settleman, et al., Nature 359: 153–4 (1992)), as may a GAP originally isolated as a CDC42Hs GAP (Hart, et al., J. Biol. Chem. 266: 20846–8 (1991); Chuang, et al., J. Biol. Chem. 268: 775–778 (1993)). The relationships and similarities between Rac1, Rac2 and CDC42Hs, as well as the predicted amino acid sequences of these molecules, is discussed in Heyworth, et al., Mol. Biol. Cell 4: 261–9 (1993), incorporated herein by reference.

These peptides, proteins, and analogs are thus useful according to the present invention in inhibiting or otherwise regulating NADPH oxidase activity. For example, FIG. 1 illustrates inhibition of NADPH oxidase activity by various peptides in dose/response conditions. According to FIG. 1, NADPH inhibition was most dramatic when mastoparan and Rac1 COOH-terminal peptide aa178–188 were administered, while a less significant amount of inhibition was observed when CDC42 COOH-terminal peptide, Gi#2 control, or Rac1 COOH-terminal peptide aa161–172 were utilized.

FIG. 2 shows the NADPH-inhibitory activity of a variety of Rac peptides, wherein percent inhibition is plotted against peptide concentration in µM. Inhibition of NADPH oxidase activity by protein p190 complexed with GAP is demonstrated in FIG. 3, wherein superoxide production is plotted against concentration of p190-GAP, with and without added GTPγS (10 µM GTPγS).

FIG. 3 illustrates the effect of p190 GAP on NADPH oxidase activity in the presence and absence of GTPγS. The concentration of p190 GAP (in µM; horizontal axis) is plotted against superoxide production (percent of control activity; vertical axis). Recombinant p190 GAP was added to reaction mixtures to give the final concentrations indicated, one minute prior to activation of $O_2^-$ production with SDS. Reaction mixtures contained $4 \times 10^5$ cell eq membranes and $1.8 \times 10^6$ cell eq of either normal cytosol (open circles, closed circles) or dialyzed cytosol (closed triangles). The final concentrations of endogenous GTP contributed by this amount of normal and dialyzed cytosol were 2.8 µM and <0.02 µM, respectively. Reactions were either performed at 2.8 µM GTP (open circles), or were supplemented with 10 µM GTPγS (closed circles, closed triangles). The control rate of $O_2^-$ production was 26.7±3.2 (S.D., n=4) nmol/min/ $10^7$ cell eq membranes. Data shown are representative of at least two experiments.

Other GDIs and their analogs may also be useful according to the present invention. (See, e.g., Hiracha, et al., Biochem. Biophys. Res. Commun. 182: 921–930 (1992); Leonard, et al., J. Biol. Chem. 267: 22860–22868 (1992); Lelias, et al., PNAS USA 90: 1479–1483 (1993).)

F. Formulations

The various peptides, derivatives and analogs of the present invention (collectively, "peptides") can be formulated into various forms for internal or external administration and application—e.g., for oral, intra-articular, intramuscular, intravenous, parenteral, subcutaneous, or rectal administration or application—in order to achieve the desired results. The peptides of the present invention may be administered via suspensions, dispersions, emulsions, lotions, creams, liquids, suppositories, capsules and other oral dosage formats, and even suppositories. Depending on the form and mode of administration, formulations may further include fillers, binders, carriers, excipients, and may be fashioned into appropriate dosage forms, each comprising a fraction or a multiple of the daily dose recommended or required to achieve the desired result.

For local administration, the peptides may be present in carrier or excipient at concentrations of about 0.1 to 1.0 mg/ml, more preferably at 0.1 mg/ml. For intra-articular injection, a preferred dose may be administered in about 1–2 ml of carrier, and preferably comprises 0.1 to 3 mg/ml, or more preferably 0.5 to 2.0 mg/ml of active ingredient (peptide).

Intravenous delivery of peptide may be required for systemic treatment. For such systemic treatment the amount of active ingredient in each administration form typically lies between 0.1 and 1 g, which may be given in preparations comprising between about 1 and 95 percent by weight of the active ingredient, the balance comprising auxiliary agents. Liquid administration forms may be prepared from concentrated forms by adding physiologically acceptable carriers or diluents such as water, saline, glucose solutions, and the like, optionally comprising buffering agents and salts rendering the final liquid preparation isotonic.

Peptides of the present invention may also be incorporated into liposomal vesicles; one useful method is that described for the incorporation of amphotericin B into lipid vesicles. (See, e.g., Lopez-Berenstein, et al., *J. Infect. Dis.* 151: 704–710 (1985); Lopez-Berenstein, et al., *Antimicrob. Agents Chemother.* 31: 675–8 (1987); Lopez-Berenstein, et al., *J. Infect. Dis.* 150: 278–283 (1984); and Mehta, et al., *Biochem. Biophys. Acta* 770: 230–4 (1984).)

Other useful methods according to the present invention include the following. In one preferred embodiment, the active ingredient (peptide) is removably inserted into a liposome, i.e., incorporated (anchored) into the liposome bilayer via the LDL binding moiety. (See, e.g., Gregoriadis, *Trends in Biotech.*, 3: 235–241 (1985) and Eriksson et al., in *Liposome Technology* Vol. II, G. Gregoriadis (ed.), CRC Press, Boca Raton, Fla., pp. 141–156. The disclosures of these articles are incorporated herein by reference.) Peptides and compositions according to the present invention can be administered in a liposome (micelle) formulation which can be administered by application to mucous membranes of body cavities. Juliano et al., *J. Pharmacol. Exp. Ther.* 214: 381 (1980). Liposomes are prepared by a variety of techniques well known to those skilled in the art to yield several different physical structures, ranging from the smallest unilamellar vesicles of approximately 20 to 50 nanometers in diameter up to multilamellar vesicles of tens of microns in diameter. Gregoriadis (ed.), *Liposome Technology* 1, CRC Press (1984). Therapeutic peptides and compositions for delivery intranasally are preferably hydrated with a lyophilized powder of multilamellar vesicles to form liposomes containing the peptides and compositions according to the present invention. Delivery may also be accomplished using liposomes with enhanced circulation time (see U.S. Pat. No. 5,013,556) and may also be targeted to specific cell types (see European Pat. No. 0,179,444). The disclosures of the cited art are incorporated by reference herein.

The amount of active ingredient (peptide) incorporated into liposomes may be about 0.1 µg active ingredient per mg lipid to about 1 mg per mg lipid. The dosage amount of active ingredient administered in lipid encapsulated form is preferably about 0.1–1 mg per mg lipid. The dosage amount of peptide administered in lipid encapsulated form may also be essentially identical to the injection route dosages indicated herein.

In another embodiment, a peptide of this invention, preferably a peptide corresponding or substantially homologous to a formula shown in Table 1 or 2 (or an analog thereof) is used in a pharmaceutically acceptable aqueous diluent composition to form an inoculum that, when administered in an effective amount, is capable of inhibiting or preventing activation of NADPH oxidase and other enzyme systems involved in the oxidative burst of phagocytic cells. The word "inoculum" in its various grammatical forms is used herein to describe a composition containing a peptide of this invention as an active ingredient used for the preparation of injectable therapeutic compositions.

The term "unit dose" as it pertains to the inocula of the present invention refers to physically discrete units suitable as unitary dosages for animals, each unit containing a predetermined quantity of active material calculated to produce the desired effect in association with the required diluent—i.e., carrier, or vehicle. The specifications for the novel unit dose of an inoculum of this invention are dictated by and are directly dependent on (a) the unique characteristics of the active material and the particular therapeutic effect to be achieved, and (b) the limitations inherent in the art of compounding such active material for therapeutic use in animals, as disclosed in detail herein, these being features of the present invention.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration. Alternatively, continuous intravenous infusion sufficient to maintain therapeutically effective concentrations in the blood are contemplated. Therapeutically effective blood concentrations of peptides of the present invention are in the range of about 0.1 µM to about 1000 µM, preferably about 0.1 µM to about 100 µM, and more preferably, about 1 µM to about 10 µM.

The peptide-containing compositions administered may take the form of solutions or suspensions; however, polypeptides can also take the form of tablets, pills, capsules, sustained release formulations or powders. In any case, the polypeptide-containing compositions typically contain about 0.1 µM to about 1.0M of polypeptide as active ingredient, preferably about 1.0 µM to about 10 millimolar (mM). Concentrations of active ingredient per amount of carrier or excipient may also be comparable to those for local or intra-articular administration.

The preparation of therapeutic compositions that contain polypeptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide can be formulated into the therapeutic composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-containing compositions may be conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject to utilize the active ingredient, and the degree of enzyme inhibition desired. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration.

Alternatively, continuous intravenous infusion sufficient to maintain therapeutically effective concentrations in the blood are contemplated. For a subject polypeptide, therapeutically effective blood concentrations are in the range of about 0.1 µM to about 10 mM, preferably about 50 µM to about 1.0 mM.

The within-disclosed and peptides were synthesized according to standard methods, as described in Section II.C. above.

EXAMPLES

The following examples are intended to illustrate, but not limit, the present invention.

Example 1

Production of $O_2^-$ in a Cell-Free System

Production of $O_2^-$ by NADPH oxidase may be monitored in a cell-free system at 25° C. by following the superoxide dismutase (SOD)-inhibitable reduction of cytochrome c at 500 nm, as described in Curnutte, et al., *PNAS USA* 86: 825–829 (1989). The method may be described essentially as follows.

Activation of the dormant respiratory burst oxidase in a cell-free system by SDS in the presence of cytosol (or partially-purified cytosol factor components) was monitored by measuring $O_2^-$ production by the activated oxidase. $O_2^-$ generation was determined by a continuous assay in which superoxide dismutase-inhibitable cytochrome c reduction was followed with time at 25° C. in a double-beam spectrophotometer at 550 nm by a modification of the method described in Curnutte, et al., *J. Biol. Chem.* 262: 6450–6452 (1987). Assay mixtures contained (final concentration) 0.15 mM cytochrome c, 6.5 mM $MgCl_2$, 87 mM KCl, 2.6 mM NaCl, 8.7 mM PIPES (pH 7.3), 0.27 mM ATP (Sigma), 0.33 mM EGTA, 0.16 mM NADPH, and 0.04 mM SDS, plus $0.9 \times 10^7$ cell eq of cytosol and $1.55 \times 10^6$ cell eq of membranes solubilized in deoxycholate (0.94 mM) in 375 µl. The reference cuvette also received 22.5 µg of superoxide dismutase. All components except NADPH were mixed in the cuvette and allowed to stand for 3.5 minutes to allow activation of the oxidase by SDS. Reactions were then started with NADPH and followed at 550 nm on a Uvikon 810 dual-beam recording spectrophotometer (Kontron, Zurich). Data were collected on a strip chart recorder and the maximal velocity of the reaction, which occurred during the first 20 sec, was used to calculate the oxidase activity.

A modification of the above-noted method was used for most of the studies described herein and may be summarized as follows. Reaction mixtures (generally, in 96-well microtiter plates) typically contain 0.1 mM cytochrome c, 6.5 mM $MgCl_2$, 87 mM KCl, 2.6 mM NaCl, 8.7 mM PIPES (pH 7.3), 10 µM GTPγS, 0.16 mM NADPH, and $4 \times 10^5$ cell equivalents (cell eq) of neutrophil membranes (about 1.6 µg protein), in a total volume of 150 µl. In addition, reactions contain varying amounts of recombinant LMWG protein, and either (1) 8 µl ($7.2 \times 10^5$ cell eq.; about 18 µg protein) of neutrophil cytosol, or (2) 100 nM each of baculovirus recombinant p47-phox and p67-phox as specified herein. Control wells (paired with each reaction well) contained 9 µg SOD, to account for non-$O_2^-$-dependent reduction of cytochrome c. Superoxide production is initiated by the addition of SDS to give a final concentration of either 90 µM (with recombinant p47-phox/p67-phox) or 110 µM (with neutrophil cytosol). Maximum rates of absorbance change, calculated from the first derivative of the time course using Softmax software (Molecular Devices, release 2.01, Menlo Park, Calif., were converted to nmol $O_2^-$ generated/min/$10^7$ cell eq of membrane, after subtracting the rate achieved in the presence of SOD from that obtained in its absence, to give the rate of $O_2^-$-dependent cytochrome c reduction, by using an extinction coefficient of 20.5 $mM^{-1}$ $cm^{-1}$ for reduced minus oxidized cytochrome c, a value determined experimentally for the 550±1-nm filter used in the kinetic microplate reader and the path length of the 250-µl reaction mixture. (See, e.g., Curnutte, et al., *PNAS USA* 86: 825–829 (1989).

Example 2

Assay Methods

A. $O_2^-$ Assays with Cells or Subcellular Fractions $O_2^-$ formation by HL-60 cells was assessed by the SOD-sensitive reduction of cytochrome c. Cells were suspended at $1 \times 10^7$/ml in Krebs-Ringer Hepes buffer with 5.5 mM glucose (KRHG) and 50–100 µl of cells were added to a cuvette containing 100 µM cytochrome c (type III, Sigma Chemical Co., St. Louis, Mo.), ±300 µg/ml SOD (Sigma Chemical Co., St. Louis, Mo.) in 700–750 µl KRHG. Cytochalasin b (Sigma Chemical Co., St. Louis, Mo.) was added to a final concentration of 5 µg/ml, and the cells were incubated at 37° C. for five minutes while a stable baseline at a wavelength of 550nm was obtained. $O_2^-$ formation was initiated by the addition of 1 µM N-formylmethionylleucylphenylalanine (FMLP; Sigma Chemical Co., St. Louis, Mo.) or 1 µg/ml phorbol myristate acetate (PMA; Sigma Chemical Co., St. Louis, Mo). Cytochrome c reduction at 550 nm was continuously monitored and maximal rate and extent of the reaction calculated.

To assess $O_2^-$ formation using HL-60 membrane and cytosol, the cell-free system of Curnutte, et al. (Curnutte, et al., *J. Biol. Chem.* 262: 5563–5569 (1987); Curnutte, et al., *J. Biol. Chem.* 262: 6450–6452 (1987)) was utilized. Briefly, HL-60 membrane pellet (50–60 µg) or human neutrophil membrane (6.35×10$^6$ cell equivalents) was added to a cuvette containing 100 µM cytochrome c (type III, Sigma Chemical Co., St. Louis, Mo.), 6.25 mM $MgCl_2$, 93 mM KCl, 2.8 mM NaCl, 9.3 mM Pipes pH 7.3, 0.8 mM ATP, 0.16 mM NADPH, 10 µM GTPγS, 225 µg HL-60 cytosol, or 250 µg (1×10$^7$ cell equivalents) of human neutrophil cytosol and ±300 µg/ml SOD (Sigma Chemical Co., St. Louis, Mo.). After a three-minute equilibration at 25° C., the formation of $O_2^-$ was initiated by the addition of 100 µM SDS. $O_2^-$ generation was monitored continuously as the SOD-sensitive reduction of cytochrome c at 550 nm. Human neutrophil plasma membranes (γ-GSP) and cytosol (GSS) were prepared as described in (Curnutte, et al., supra (1987)). Quantification of GTP-binding proteins is determined as described in Heyworth, supra (1993).

B. Flow Cytometric Analysis of Cell Viability

Cell viability was determined by uptake of propidium iodide (537–059; Calbiochem-Behring Corp., La Jolla, Calif.), detected from the emission fluorescence at 625/35 nm using a DM560 dichronic mirror (Krishan, *J. Cell. Biol.* 66: 188–192 (1975)). Expression of N-formyl peptide receptor was determined using fluorescein-labeled N-CHO-Xaa-leu-Phe-Xaa-Try-Lys, where Xaa is the modified amino acid, Nle (SEQ ID NO 25) (Molecular Probes, Inc., Eugene, Oreg.) essentially by the method of Sklar and Finney (Sklar and Finney, *Cytometry* 3: 161–165 (1982)). Specificity of ligand binding was determined in the presence of 4 mM unlabeled T-boc peptide. CD14 expression was determined using monoclonal antibody 3C10 at a dilution of 1:1,000 (see Goyert and Ferrero, in *Leucocyte Typing III: White Cell Differentiation Antigens*, McMichael, ed., Oxford Univ. Press, NY, pp. 613–619 (1988)), with detection using a fluorescein-labeled secondary antibody. Flow cytometric analyses were performed on a FACS IV (registered trademark of Becton-Dickinson, San Jose, Calif.) equipped with a 2 W argon laser (Coherent Inc., Palo Alto, Calif.) using a flow rate of <1,000 cells/sec. Data were collected in list mode and analyzed using the Consort 30 program (Becton-Dickinson, San Jose, Calif.) after collecting 10,000 events.

C. Immunological Procedures

Western blots were performed as described in Bokoch, et al., *Cell Biol.* 106: 1927–1936 (1988). Anti-Rap1 antibody R61, anti-G protein β subunit antibody R3.4, and anti-cytochrome 22-kD subunit antibody are all specific and are described in Bokoch, et al., *Cell Biol.* 106: 1927–1936 (1988); Quilliam, et al., *J. Immunol.* 147: 167 (1991); Parkos, et al., *J. Clin. Invest.* 80: 732–742 (1987), respectively.

Analysis of Rap1 processing in HL-60 cells was performed by labeling cells (8×10$^5$/ml) with 200 µCi/ml $^{35}$S-Trans-label (ICN Biomedicals, Inc., Costa Mesa, Calif.) for 5 days during cell differentiation with 1.3% DMSO in Cys-Met-free medium containing 12% dialyzed fetal bovine serum. Metabolically labeled cells were collected, washed once with isotonic NaCl, treated with 2.5 mM Hepes pH 7.5, 100 mM NaCl, 1 mM EDTA, 1% Triton X-100, 2.5µM PMSF, and 100 U aprotonin. After a 15-minute incubation on ice, the cell lysates were pelleted in a microfuge for 2 minutes and then the supernatant was transferred to clean tubes containing 100 µl 4M NaCl, 5 µl 10% SDS, and 50 µl 10% deoxycholate. The samples were boiled for two minutes, pelleted, and transferred to clean tubes containing 2 µl of the primary antibody, 142–24E05 (Chesa, et al., *PNAS USA* 84: 3234–3238 (1987); Bokoch, et al., *J. Biol. Chem.* 263: 16744–16749 (1988)). Immune precipitates were then worked up as previously described (Quilliam, et al., *J. Immunol.* 147: 167 (1991)), except that the pellets were washed six times with 1ml 50 mM Hepes pH 7.5, 500 mM NaCl, 0.1% Triton X-100, and 0.059% SDS before preparation for SDS-PAGE.

D. SDS Gel Electrophoresis and Silver Staining

SDS polyacrylamide gel electrophoresis and silver staining were performed using previously described methods (Knaus et al., Id., 1992). Reagents used in the purification of neutrophils, the preparation of neutrophil fractions and the cell-free O2- assay were obtained from the sources previously reported (Curnutte et al., 1987). [$^{35}$S]GTPγS was from du Pont-NEN Research Products (Boston, Mass.). Lysozyme (from egg white, 20,000 Units/mg) was obtained from United States Biochemical Corp., Cleveland, Ohio. Deoxyribonuclease I (from bovine pancreas) was purchased from Sigma Chemical Co., St. Louis, Mo.

E. Preparation of Neutrophils, Membranes and Neutrophil Subcellular Fractions

Purification of neutrophils (typically obtained via leukapheresis) is generally carried out via the procedures described in Curnutte, et al., *J. Biol. Chem.* 262: 5563–5569 (1987) or *J. Clin. Invest.* 83: 1236–40 (1989), although dextran sedimentation may be omitted. The procedure is essentially as follows.

Neutrophils are prepared as described in Badwey, et al., *Biochem. Biophys. Res. Commun.* 106: 170–174 (1982), using Sigma dextran (6% (w/v) in 0.155M NaCl) as the sedimenting agent, and suspended in Dulbecco's calcium- and magnesium-free phosphate-buffered saline (PBS). The cells were treated with diisopropyl fluorophosphate (DFP) by the method of Crowley, et al. (*NEJM* 302: 1163–1168 (1980)) except that phosphate was omitted from the buffer and the DFP concentration was reduced to 2.5 mM. DFP-treated cells (which may be pooled from one or more donors) were disrupted by $N_2$ cavitation, and fractionated on a discontinuous Percoll gradient by a modification of the method of Borregaard, et al. *J. Cell. Biol.* 97: 52–61 (1983).

Membranes are obtained from the Percoll gradient by pooling the gamma fraction (see Borregaard, Id.) with a high-speed (230,000 ×g for 2 hours at 4° C.) pellet from the cytosolic fraction. The membranes were suspended at a concentration of 1.25×10$^9$ cell eq/ml (4.0±0.9 S.D. mg protein/ml (n=3)) in half-strength Borregaard's relaxation buffer (50 mM KCl, 1.5 mM NaCl, 5 mM PIPES (pH 7.3), 1.75 mM $MgCl_2$, 0.5 mM ATP, 0.62 mM EGTA) containing 0.34M sucrose. The suspension was divided into aliquots and stored at −70° C. The supernatant from the 230,000 × g spin (designated "cytosol"), which contained 7.5×10$^7$ cell eq/ml (1.3 ±0.2 S.D. mg protein/ml (n=3)), was divided into aliquots and stored at −70° C.; this material served as a source of cytosolic activation factor.

Membranes are solubilized by a modification of the procedure described by Glass, et al., *J. Biol. Chem.* 261: 13247–13251 (1986). The membrane suspension was thawed at room temperature, mixed with an equal volume of extraction buffer (1 mM $NaN_3$, 0.0017 mM $CaCl_2$, 20 mM sodium glycinate (pH 8.0), 2.33% sodium deoxycholate (w/v), and 50% glycerol (v/v), vortexed briefly, incubated on ice for 30 minutes with occasional agitation, and finally centrifuged at 435,000×g for 1 hour at 4° C. (Beckman TL-100 tabletop ultracentrifuge with a TL-100.2 rotor, using polycarbonate tubes). The dormant oxidase was found in the supernatant, whose protein concentration was 1.3±0.4 S.D. mg/ml (n=3). The oxidase-containing supernatant was stored on ice and discarded at the end of the day.

Protein concentration was measured by the method of Smith, et al., *Anal. Biochem.* 150: 76–85 (1985), using the bicinchoninic acid protein assay reagent from Pierce Chemical Co.

Neutrophil yields tend to be about $0.9$–$2.2 \times 10^{10}$ cells per donor. Neutrophils may also be prepared from whole blood obtained by venipuncture as described (Id.). Cytosol and deoxycholate-solubilized membranes were then prepared as described in Curnutte, et al., *J. Biol. Chem.* 262: 6450–6452 (1987) and Babior, et al., *J. Biol. Chem.* 263: 1713–1718 (1988).

Protein concentrations of these fractions have been reported to be as follows: for cytosol, 250±16 μg per $10^7$ cell eq (mean ± SEM) and for deoxycholate-solubilized membranes, 25.7±1.4 μg per $10^7$ cell (mean ± SEM). The volumes of cytosol preparations are generally adjusted so they contain $9 \times 10^7$ cell eq per ml. (See Babior, et al., Id.)

Example 3

Assays to Determine the Inhibitory Activity of Antibodies and Peptides

Peptides were tested for oxidase inhibiting activity using the cell-free assay of Curnutte, et al. (*PNAS USA* 86: 825–829 (1989)). Peptides were added at indicated concentrations and incubated for five minutes at room temperature prior to initiation of $O_2^-$ formation using either 90 μM SDS or 100 μM arachidonic acid as an activating stimulus.

Table 3 lists a panel of peptides utilized for $O_2^-$ activity tests (see Table 1) and their ascertained NADPH oxidase modulating activity. (SEQ ID NOS for the following peptides are given in Table 1.)

TABLE 3

| Peptide | Peptide Sequence | Inhibitory Activity |
|---|---|---|
| Rac1 aa178–188 | CPPPVKKRKRK | Active |
| Rac1 aa161–172 | LTQRGLKTUFDE | Inactive |
| Rac1 aa127–137 | EKLKEKKLTPI | Inactive |
| Rac2 aa178–188 | CPQPTRQQKRA | Active |
| Rap1B aa172–180 | PGKARKKSS | Active |
| Rap1A aa172–180 | EKKKPKKKS | Active |
| Mastoparan | INLKALAALAKKIL | Active |
| $G_i$ #2 | SKFEDLNKRKDT | Inactive |
| $G_i$ #5 | MGCTVSAEDKAAAER | Inactive |
| CDC42Hs | KNVFDEAILAALEPP-EPKKSRR | Inactive |
| ICS4 | GLAQKLLEALQKALLA | Active |
| ECG 125 | GELAQKLEQALQKLA | Inactive |
| ECG 163 | GEHAQKHEQALQKLA | Inactive |

TABLE 3-continued

| Peptide | Peptide Sequence | Inhibitory Activity |
|---|---|---|
| ARF 26 | $NH_2$-terminal helix | Low Activity |
| ARF 27 | $NH_2$ Δ2 | Low Activity |
| ARF 28 | $NH_2$ Δ4 | Low Activity |

Figure 4:
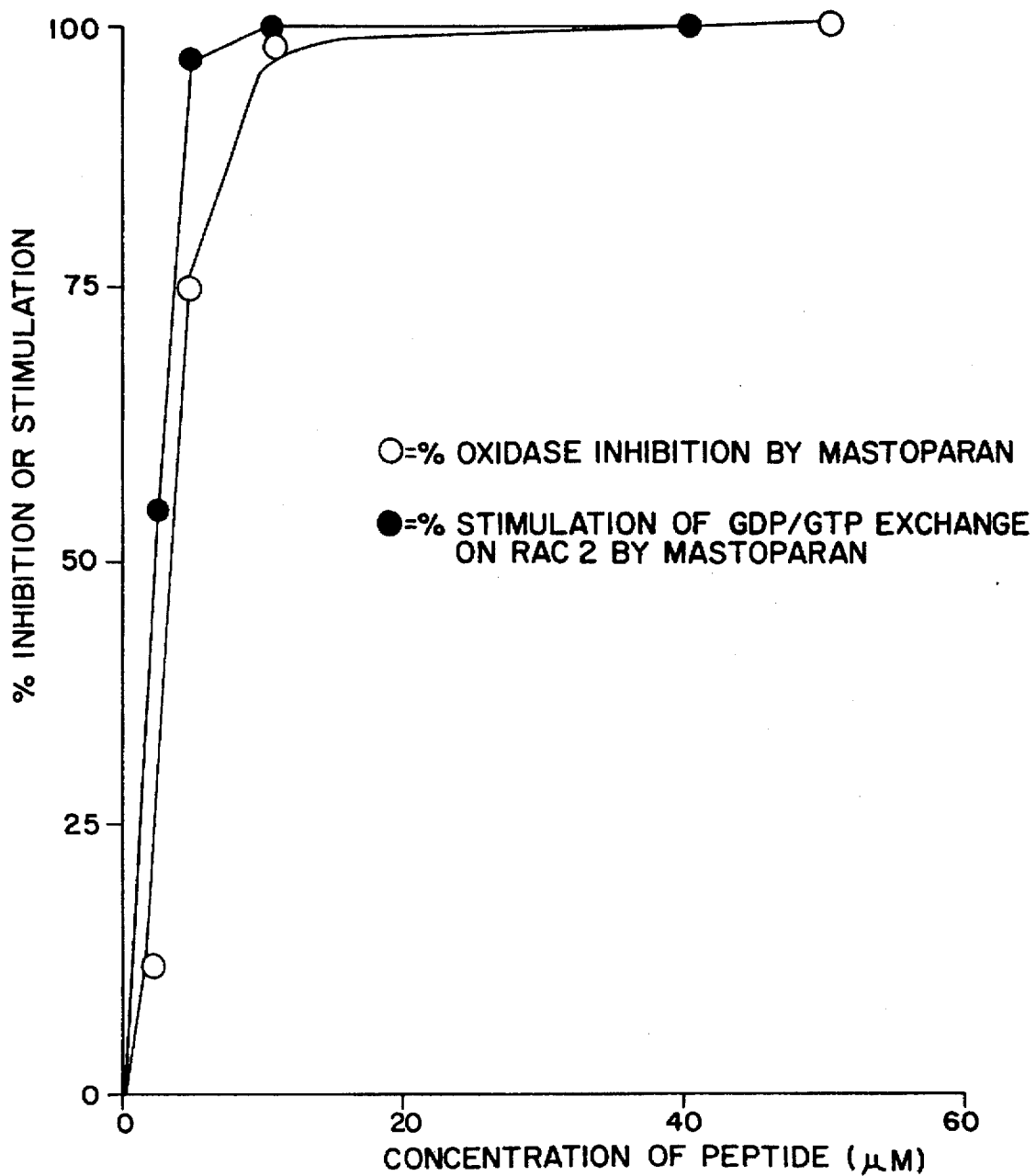
FIG. 4 illustrates the ability of mastoparan and analogs to stimulate guanine nucleotide exchange (GDP/GTP exchange) on Rac2 protein (closed circles), as well as to inhibit NADPH oxidase (open circles). The concentration of the peptide is indicated on the horizontal axis (in μM), whereas percent inhibition or percent stimulation are indicated on the vertical axis.
Figure 5:
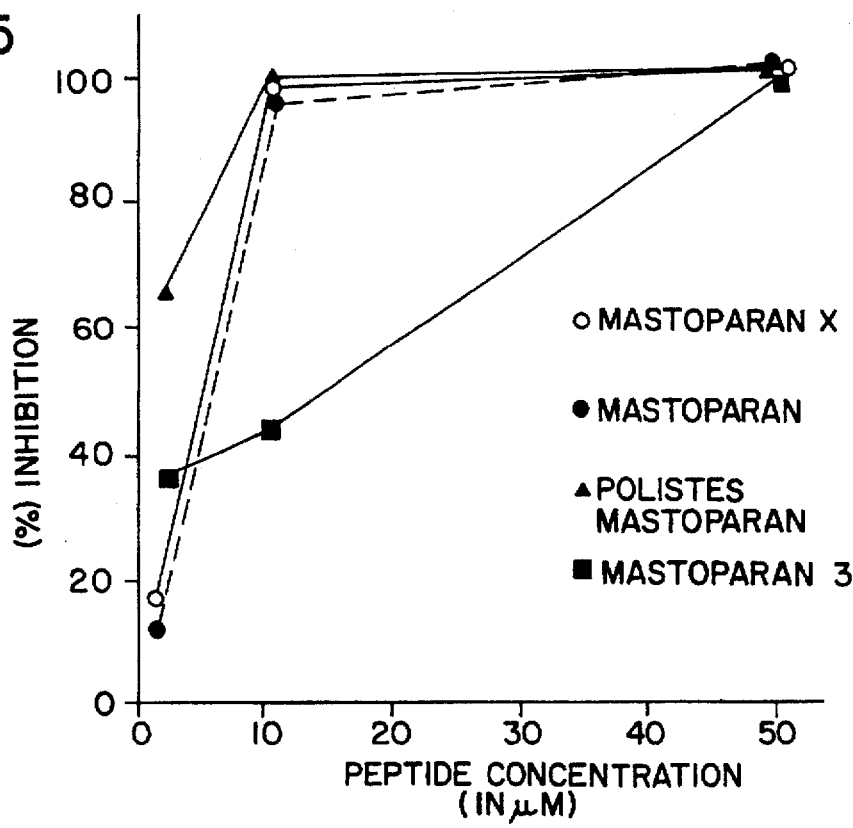
FIG. 5 illustrates the effects of mastoparan and its analogs on NADPH inhibition, ascertained via determination of $O_2^-$ production in a cell-free system. Data for mastoparan (closed circles), mastoparan X (open circles), mastoparan Polistes (closed triangles), and mastoparan 3 (closed squares) are shown, with peptide concentration (in μM) indicated on the horizontal axis and percent inhibition on the vertical axis.

FIG. 4 illustrates the ability of mastoparan and mastoparan analogs to stimulate guanine nucleotide exchange on Rac protein (closed circles), as well as to inhibit NADPH oxidase (open circles). The concentration of the peptide is indicated on the horizontal axis, whereas percent inhibition/percent stimulation are indicated on the vertical axis. In FIG. 5, the effects of mastoparan and its analogs on NADPH inhibition, ascertained via determination of $O_2^-$ production in a cell-free system, are shown. Data for mastoparan (closed circles), mastoparan X (open circles), mastoparan Polistes (closed triangles), and mastoparan 3 (closed squares) are shown, with peptide concentration (in μM) indicated on the horizontal axis and percent inhibition on the vertical axis.

Studies on the inhibition of NADPH oxidase measured in a cell-free system (as described above) also illustrates a correlation between increasing concentrations of various peptides and percent inhibition. Results are set forth in Table 4 below.

TABLE 4

| | Percent Inhibition | | |
|---|---|---|---|
| Peptide | 27 μg/ml | 100 μg/ml | 200 μg/ml |
| ICS4 | 86.8 | 99.8 | |
| ECG125 | | 23.3 | 34.0 |
| ECG163 | | 8.0 | 5.1 |
| ARF 26 | 30.9 | 100 | |
| ARF 27 | 55.9 | 91.3 | |
| ARF 28 | 43.5 | 87.6 | |

Antibodies to peptides according to the present invention may also be useful NADPH oxidase inhibitors and may be prepared essentially as described herein. Antibodies to the COOH-terminal peptides derived from Rac1 and Rac2 are described as exemplary, but it is expressly to be understood that the described methodology is operable for antibodies to other within-disclosed peptides, as well.

Affinity-purified antibodies to COOH-terminal peptides specific for Rac1 and Rac2 were prepared according to known methods; see, e.g., Bokoch, et al., *Cell Biol.* 106: 1927–1936 (1988); Quilliam, et al., *J. Immunol.* 147: 167 (1991); or Malech, et al., published PCT application No. WO91/17763. While the antibodies used herein were generated in rabbits, useful antibodies may be generated using other known mammals. (See, e.g., U.S. Pat. Nos. 5,149,780 and 5,196,511 of Plow, et al., which describe generation of antibodies using murine species.) Similarly, useful antibodies according to the present invention may be monoclonal or polyclonal.

Antibody to Rac1 was generated to the peptide CPPPVKKRKRK (SEQ ID NO 11) and used in a 1:100 dilution for protein immunoblots. Antibody to Rac2 was generated to the COOH-terminal peptide CPQPTRQQKRA (SEQ ID NO 12) and used in a 1:150 dilution. Bound antibody was detected with $^{125}$I-labeled goat antibody to rabbit IgG. Antibodies produced to both peptides were isolated and affinity purified prior to use.

Figure 6:
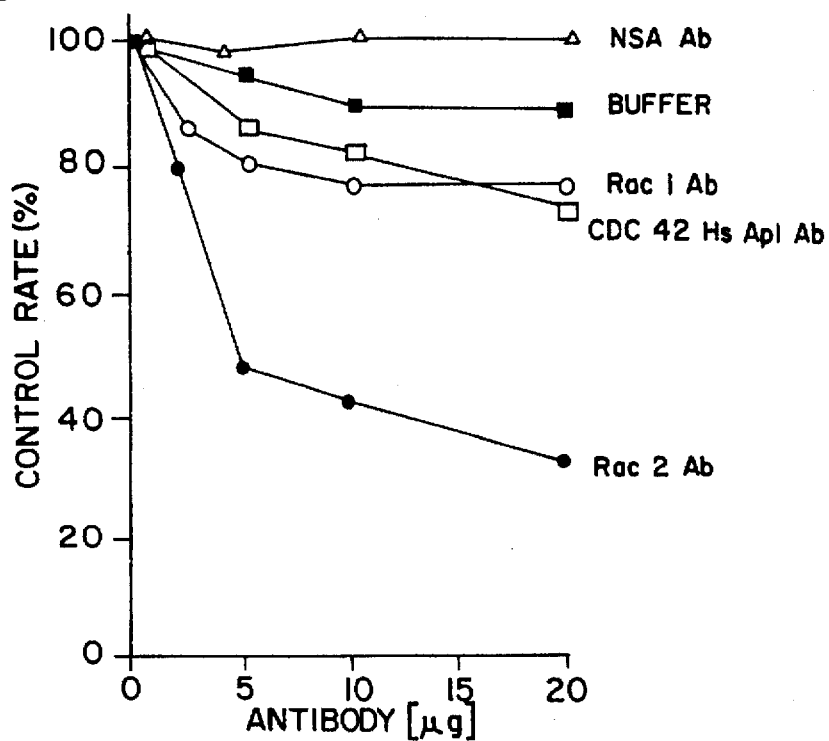
FIG. 6 illustrates the inhibition of NADPH oxidase by antibodies to various peptides described herein. Antibodies specific to Rac2 (closed circles), to Rac1 (open circles), to CDC42Hs Ap1 (open squares), to an undefined neutrophil surface antigen (NSA, open triangles) were tested, as was the buffer in which the affinity-purified antibodies were dissolved (closed squares). Antibody concentration in micrograms (μg) is indicated on the horizontal axis, whereas control rate expressed as a percentage is indicated on the vertical axis.

Each antibody was then assayed for its ability to inhibit NADPH oxidase. Human neutrophil cytosol was incubated for 16 hours at 4° C. with varying amounts of affinity purified antibody, as shown in FIG. 6. The mixtures of cytosol and antibody were then assayed in the cell-free oxidase assay (150 μl) as described in Curnutte, et al., *PNAS USA* 86: 825 (1989). The amount of cytosol used in the assay ($2\times10^6$ cell equivalents) was sufficient to support about 95% of the maximal rate obtainable. Results are expressed as a percentage of the rate of $O_2^-$ formation in the absence of antibody or antibody buffer and are indicative of at least three experiments (see FIG. 6).

Control values of $O_2^-$ generation varied from 30 to 50 nmol/min/$10^7$ cell equivalents of membrane in individual experiments. Antibodies specific to Rac2 (closed circles) and Rac1 (open circles) were prepared with peptides representing amino acids 178–188 of each protein, as described above. Also tested were antibody to CDC42Hs Ap1 (open squares); Ap1 is an affinity-purified antibody to the COOH-terminal peptide NVFDEAILAALEPPEPK (SEQ ID NO 20 from position 1 to 18) from CDC42Hs and was used in a 1:500 dilution on protein immunoblots. (See Polakis, et al., *Biochem. Biophys. Res. Commun.* 160: 25 (1989).) Monoclonal antibody to an undefined neutrophil surface antigen (open triangles) was also tested, as was the buffer in which the affinity-purified antibodies were dissolved (closed squares). That buffer comprised 200 mM glycine neutralized to pH 7.5 with phosphate buffer.

The results illustrated in FIG. 6 demonstrate that antibody to Rac2 caused a concentration-dependent inhibition of $O_2^-$ generation that, at the highest concentration tested, resulted in 70% inhibition. This effect was partially reversed by preincubation of the Rac2 antibody with $G_{ox}$ protein, although experiments were limited by the small amount of the GTP-binding protein available. In contrast, antibodies to the Rac1 and CDC42Hs COOH-terminal peptides showed some inhibitory activity, albeit much less than that of the antibody to Rac2. An antibody to an undefined neutrophil surface antigen also did not inhibit $O_2^-$ generation.

Example 4

Regulation of NADPH Oxidase Activity Using Rac GAP Proteins

A. Preparation of Proteins and Vectors

Recombinant Rac1 and Rac2 were prepared and purified from the membranes of baculovirus-infected Sf9 insect cells as described previously in Heyworth, et al., *Mol. Biol. Cell* 4: 261–269 (1993) (the disclosures of which are incorporated by reference herein). These proteins are post-translationally isoprenylated and processed, and are fully active in GTP binding and NADPH oxidase assays.

The Rac2 (Q61L) mutant was prepared, expressed in Sf9 cells, purified, and characterized essentially as follows. First, appropriate *E. coli* expression vectors were constructed. Two oligonucleotides, 5'-GGG GGA AGC TTC ATA TGC AGG CCA TCA AGT GTG-3'(SEQ ID NO 26), which contained a NdeI site at the initiator methionine codon in the Rac2 cDNA, and 5'-GGG GGG GGA TCC TAG AGG AGG CTG CAG GCG CG-3'(SEQ ID NO 27), which contained a BamHI site immediately after the stop codon for Rac2, were used as primers to amplify the coding sequence of Rac2 by polymerase chain reaction (PCR).

Although a PCR kit was used herein (see below), PCR amplification methods are described in detail in, for example, U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

Useful components of a PCR reaction are also readily available. For example, *Thermus aquaticus* DNA polymerase I is described in U.S. Pat. No. 4,889,818. Similarly, useful inducing agents are described in Chamberlin et al., *The Enzymes*, ed. P. Boyer, PP. 87–108, Academic Press, New York (1982) and Joyce, et al., *Nuc. Acid Res.* 17: 711–722 (1989), to name two examples. Amplification systems based on transcription have also been described by Gingeras et al., in *PCR Protocols, A Guide to Methods and Applications*, pp 245–252, Academic Press, Inc., San Diego, Calif. (1990).

The full-length coding cDNA encoding Rac2 was subcloned into the *E. coli* expression vector pET-11a (Novagen, Madison, Wis.) in NdeI/BamHI sites. The mutant Rac2 cDNAs were prepared by site-directed mutagenesis using PCR methodology. (See, e.g., Sambrook, et al., *Molecular Cloning: A Laboratory Manual*, 2d Ed., Cold Spring Harbor Lab. Press, Cold Spring Harbor, N.Y. (1989)) The PCR kit utilized herein was purchased from Perkin Elmer/Cetus (Norwalk, Conn.) and was used according to the manufacturer's instructions.

The baculovirus expression vector was prepared as follows. In order to create a baculovirus construct encoding the wild type or mutant Rac2 with an additional N-terminal sequence encoding an epitope tag, Met-Glu-Glu-Glu-Glu-Tyr-Met-Pro-Met-Glu (see (SEQ ID NO 24) Heyworth, et al., *Mol. Biol. Cell* 4: 261–269 (1993)), an oligonucleotide containing KpnI/NCOI sites at the initiator methionine codon (5'-GGG GGG GGT ACC ATG GAG GAG GAG GAG TAC ATG CCG ATG GAG CAG GCC ATC AAG TGT GTG G-3') was (SEQ ID NO 28) used as 5' primer and the oligoncleotide 5-GGG GGG GGA TCC TAG AGG AGG CTG CAG GCG CG-3' (SEQ ID NO 29)containing a BamHI site immediately after the stop codon for Rac2 was used as 3' primer to amplify the coding sequence of wild type or mutant Rac2 by PCR. The PCR product was subcloned into transfer vector pAcC13, which was derived from pAcC12 (see Summers, et al., *Texas Agr. Exp. Station Bulletin:* 1555 (1988)) by deleting 400bp of the polyhedron coding region and introducing a polylinker sequence, in KpnI/BamHI sites. All of the constructs were verified by DNA sequencing using a DNA sequencing kit purchased from U.S. Biochemical Corporation. All of the restriction enzymes utilized were purchased from Gibco/BRL Life Technologies (Grand Island, N.Y.).

*Spodoptera frugiperda* (Sf9) host cells were cotransfected with the Rac-containing transfer vector and wild-type baculovirus (AcMNPV) DNA (Summers, et al., Id. (1988)). On day four post-transfection, the media from the transfected plates was harvested as a virus stock which contains the desired recombinant virus mixed with wild type virus. Sf9 cells (at $1\times10^6$ cells/ml) were infected with the virus mix (diluted from $10^4$ to $10^{-7}$) and overlaid with 0.7% agarose (FMC) in Excell 400 insect media. After six days' incubation at 27° C., recombinant plaques were differentiated from wild type plaques by the absence of viral occlusions. Positive plaques were selected and incubated in 500 μl of Excell 400 medium at 4° C. overnight to elute the virus. Three rounds of plaque assays were usually required to purify the recombinant virus.

Rac proteins were expressed in *E. coli* or the baculovirus-insect cell system as described in Heyworth, et al., *Mol. Biol.*

Cell 4: 261-269 (1993). (See also Quilliam, et al., Mol. Cell. Biol. 10: 2901-2908 (1990); Hart, et al., J. Biol. Chem. 266: 20840-20848 (1991).) The bacterially-expressed proteins were purified by ion-exchange chromatography on a DEAE Sephacel column (Pharmacia LKB, Piscataway, N.J.). The bacterial cell pellet was resuspended in 25 mM Tris-HCl (pH 8.0), 1 mM EDTA, 5 mM MgCl$_2$, 1 mM dithiothreitol (DTT), 1 mM phenylmethylsulfonyl fluoride (PMSF) containing 0.2 mg/ml of lysozyme, and 0.1% Triton X-100, at a volume 0.25 times that of the original culture. After 15 minutes' incubation at 30° C., the suspension was subjected to 5×1 minute bursts of sonication on ice. After centrifugation for 25 minutes at 15,000×g, the supernatant was applied to a 30 ml DEAE column pre-equilibrated with 25 mM Tris (pH 7.5), 1 mM EDTA, 5 mM MgCl$_2$, 1 mM DTT, and 1 mM PMSF. The column was washed extensively with equilibration buffer (6 times the bead volume of the column) and the protein was eluted with a 150 ml linear gradient of 0-750 mM NaCl. The Rac protein was eluted at about 100 mM NaCl, and was at least 80% pure as estimated by silver staining. The purification of baculovirus recombinant proteins utilized affinity chromatography as described in Heyworth, et al., Mol. Biol. Cell 4: 261-269 (1993), and the resulting proteins were at least 90% pure.

Protein p190 was prepared and purified as described in Settleman, et al., Id. (1992). The procedures are essentially as follows. p190 protein was purified from RS-2 tumors. Soluble protein lysate was prepared from 15 g of tumor tissue by homogenization in a buffer containing 50 mM HEPES (pH 7.4), 150 mM NaCl, 1.5 mM MgCl$_2$, 5 mM EGTA, 10% glycerol, 1 mM phenylmethylsulfonyl fluoride (PMSF), 5 µg/ml aprotinin, 5 µg/ml leupeptin, 1 mM β-glycerophosphate, and 1 mM sodium orthovanadate. The lysate was clarified by centrifugation at 60,000×g for one hour, and the supernatant was added to 1 ml of protein A-Sepharose beads (50% slurry) and gently mixed for 1 hour at 4° C. as a pre-clearing step. The beads were sedimented and the supernatant was transferred to a new tube containing 1 ml of protein A-Sepharose beads that had been covalently cross-linked to 1 mg of affinity-purified anti-GAP monoclonal antibody (B4F8) with dimethylpimelimidate, and the tube was rotated at 4° C. for 4 hours. The beads were sedimented at 1 g, washed four times with 20 mM HEPES (pH 7.4), 150 mM NaCl, 0.1% Triton X-100, and 10% glycerol, and the bound protein was eluted by boiling in 1 ml of 50 mM Tris (pH 7.5), 2% SDS, 2M β-mercaptoethanol, and 5% glycerol.

The eluted protein was loaded onto a 5% SDS-polyacrylamide gel (Laemmli, Nature 227: 680-5 (1970)) and resolved by electrophoresis at 200V. The resolved proteins were transferred to nitrocellulose (Towbin, et al., PNAS USA 76: 4350-4 (1979)) in a buffer of 10 mM CAPS (pH 11.0) containing 10% methanol at 400 mA for 14 hours, and the filter was stained with Ponceau S. The p190 protein band was excised from the filter, washed extensively with water, and incubated for 30 min. at 22° C. with 0.5% polyvinylpyrrolidine-40 in 0.1M glacial acetic acid. The filter was then washed with 50 mM Tris (pH 9.0) and soaked in 8M urea for 30 min. at 37° C. One microgram of Achromobacter protease I was then added, and the sample was maintained at 37° C. for 36 hours (Riviere, et al., in Techniques in Protein Chemistry II, J. J. Villafranca, ed., Academic Press, N.Y. (1990)). The cleaved peptides were resolved by reverse-phase high pressure liquid chromatography on a narrow bore C-18 column, and the three best-resolved peaks were subjected to automated Edman degradation to determine amino acid sequence.

Generation of antibodies against GAP proteins (e.g., p190) is carried out according to known methods. For example, p190 or a portion thereof is preferably purified and used to immunize mice on a biweekly injection schedule. Sera may then be collected by tail vein bleed 10 days following the third boost, processed, and utilized as the source of anti-p190 antibody.

A method of generating useful amounts of p190 fragments—such as the carboxy-terminal region of p190, which appears to possess sequences homologous to proteins possessing an intrinsic GAP activity—is described in Settleman, et al. (Cell 69: 539-549 (1992)). For example, a 1018 bp fragment corresponding to nucleotides 1245-2263 was generated by PCR using opposing primers (5'-CGAAGGATCCGGAACTTCGATGACCAGC-3' and (SEQ ID NO 30) 5'-CGGAATTCTATTTAGCATCCAGCTCCAG-3') (SEQ ID NO 31) containing cloning sites, and the product was subcloned into the PET-5A inducible E. coli expression vector (Novagen, Madison, Wis.) to generate plasmid PET5-190. The overexpressed 45 kd fusion protein was found to be insoluble and present in inclusion bodies that were purified by sonication of the cell pellet in a solution of 50 mM Tris (pH 7.5), 3 mM EDTA, and 3 mg/ml lysozyme, followed by extraction with 1% NP-40 and 1M NaCl. The fusion protein was further purified by preparative polyacrylamide gel electrophoresis of inclusion body material, and gel slices containing approximately 50 µg of protein were used to immunize mice on a biweekly injection schedule. Sera were collected by tail vein bleed 10 days following the third boost.

CDC24Hs GAP was purified according to the method described in Hart, et al., J. Biol. Chem. 266: 20840-20848 (1991). Recombinant Sf9 cell RhoA was produced in our laboratory according to the within-described methods.

B. Assays and Methods

The [γ$^{32}$P]GTP Rac1 or Rac2 complex was formed by incubation of purified, recombinant Rac protein (150 nM) with 25 mM Tris-HCl pH 7.5, 1 mM dithiothreitol, 4.7 mM EDTA, 100 µg/ml bovine serum albumin, 10 µM GTP (10,000-15,000 cpm/pmol), and 35 nM free Mg$^{++}$ at 30° C. for four minutes. GTP hydrolysis was initiated by addition of MgCl$_2$ to 19 mM and GTP to 200 µM in the presence of the indicated concentrations of p190 GAP plus or minus 110 µM SDS. The amount of [γ$^{32}$P]GTP that remained protein-bound was determined by filtration after five minutes incubation at room temperature (Knaus, et al., J. Biol. Chem. 267: 23575-23582 (1992); Chuang, et al., J. Biol. Chem. 268: 775-778 (1993)).

Subcellular fractions from human neutrophils for use in cell-free NADPH oxidase assays were prepared as described previously (Curnutte, et al., PNAS USA 86: 825-829 (1989)). Cell-free oxidase assays were conducted as described in Heyworth, et al., Mol. Biol. Cell 4: 261-269 (1993) and Curnutte, et al., Id. (1989). In order to deplete endogenous guanine nucleotides for some experiments, cytosol was dialyzed overnight against three 2-liter volumes of 100 mM KCl/3 mM NaCl/3.5 mM MgCl$_2$/10 mM PIPES, pH 7.3, as previously described (Peveri, et al., PNAS USA 89: 2494-2498 (1992)). Reaction mixtures contained 4×10$^5$ cell equivalents (cell eq) of human neutrophil membranes and 1.8×10$^6$ cell eq of neutrophil cytosol. Reactions were performed in the absence of GTPγS, unless otherwise indicated (see FIGS. 3, 7, 8, and 9, and accompanying legends), and with the indicated concentrations of p190 GAP. Rates of O$_2^-$ production were calculated from maximum rates of absorbance change after initiation of the reaction with 110 µM SDS.

SDS-polyacrylamide gel electrophoresis was performed as previously described (Settleman, et al., Id. (1992)). Reagents used in these studies were of the highest available grade, and were obtained from the sources indicated in the cited references. GTP and GTPγS were obtained from Sigma Chemical Company (St. Louis, Mo.). [$^{35}$S]GTPγS and [γ$^{32}$P] GTP were from duPont-NEN Research Products (Boston, Mass.).

C. Results

The cDNAs encoding p190 protein have been cloned and the predicted protein product has been found to contain a region of homology with the breakpoint cluster region (Bcr) gene product associated with chronic myelogenous leukemia (CML). (See, e.g., Settleman, et al., Id. (1992); Groffen, et al., Cell 36: 93–99 (1984).) This region of Bcr exhibits GAP activity for the Rac1 protein (Diekmann, et al., Nature 351: 400–402 (1991)), and a number of proteins containing this domain have the ability to stimulate GTP hydrolysis by GTP-binding proteins of the Rho family (Bokoch and Der, FASEB J. 7: 750–759 (1993); Hall, Cell 69: 389–391 (1992) ). Indeed, p190 has been shown to have GAP activity for Rac1 and Rac2, as well as for RhoA and CDC42Hs. (See, e.g., Settleman, et al., id. (1992).)

Figure 7:
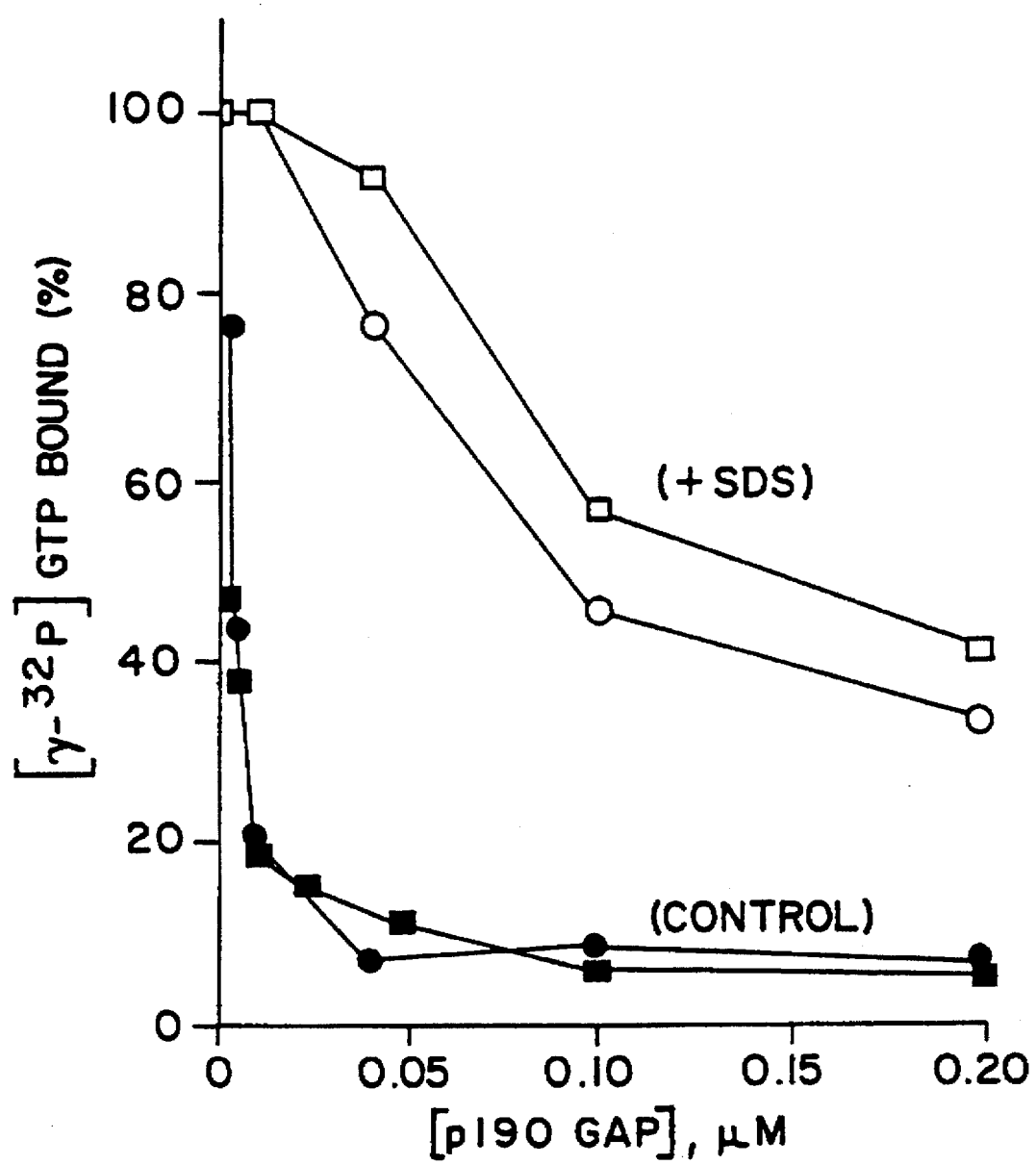
FIG. 7 illustrates the activation of Rac GTPase activity by p190 GAP. The amount of p190 GAP (in μM) is plotted on the horizontal axis, whereas the percent of [γ$^{32}$P]GTP bound is plotted on the vertical axis. Rac1 (open and closed squares) or Rac2 (open and closed circles) was loaded with [γ$^{32}$P]GTP, and GTP hydrolysis initiated in the presence of the indicated concentrations of p190, as described in Methods (Example 4 herein). Closed symbols indicate the absence of SDS (control) and open symbols indicate the presence of 110 μM SDS.

FIG. 7 shows that p190 GAP produced a concentration-dependent stimulation of the rate of GTP hydrolysis by Rac1 and Rac2. The effect of p190 GAP was antagonized by the presence of 110 μM SDS (see FIG. 7) or 150 μM arachidonic acid (data not shown). (The concentrations of SDS and arachidonic acid used in these studies are the concentrations of these anionic amphiphiles typically used in the cell-free NADPH oxidase assay.) About 10-fold more p190 was required for a given level of GAP activity when SDS or arachidonic acid was present. In contrast, the activity of CDC42Hs GAP for Rac was essentially unchanged by the presence of SDS or arachidonic acid (data not shown).

The within-described studies also confirmed the presence of p190 in human phagocytic leukocytes. Human neutrophil membranes (30 μg) or cytosol (50 μg), and DMSO-differentiated HL60 cell lysates (2×10$^5$ cell eq) were immunoblotted with a 1:1000 dilution of a p190-specific antibody as described herein and in Settleman, et al., Cell 69: 539–549 (1992). Western blots of isolated human neutrophil membranes and cytosol, as well as total lysates from HL60 promyelocytic cells which had been fully differentiated into a neutrophil-like cell by exposure to 1.25% dimethylsulfoxide for six (6) days, were prepared and examined (results not shown). The presence of p190 in human phagocytes could be seen after immunoblotting with a p190-specific antibody (Settleman, et al., Cell 69: 539–549 (1992); Settleman, et al., Nature 359: 153–154 (1992)). p190 was found to be primarily localized to the neutrophil cytosol, although a small amount could be detected in the purified plasma membrane function.

The ability of Rac to stimulate NADPH oxidase activity is dependent upon Rac being in the GTP-bound state. (See, e.g., Mizuno, et al., J. Biol. Chem. 267: 10215–10218 (1992); Kwong, et al., Biochemistry 32: 5711–5717 (1993); Heyworth, et al., Mol. Biol. Cell 4: 261–269 (1993); Abo, et al., Nature 353: 668–670 (1991).) In order to investigate whether GAP proteins which are able to modulate the GTP/GDP state of Rac could regulate NADPH oxidase activity, the effect of adding p190 GAP to a cell-free NADPH oxidase assay was examined (see FIG. 3). The addition of recombinant p190 GAP to the system one minute before initiation of the reaction with SDS resulted in a concentration-dependent inhibition of $O_2^-$ formation, with half-maximal inhibition occurring at about 100 nM p190 GAP. This correlates well with the amount of p190 GAP required for half-maximal stimulation of Rac GTPase activity in the presence of SDS (see FIG. 7). The inhibitory effect of p190 GAP in the cell-free system was substantially reversed by the addition of 10 μM GTPγS (FIG. 3). Since the free GTP concentration in the whole cytosol reaction is estimated to be 2.8 μM (Peveri, et al., PNAS USA 89: 2494–2498 (1992)), it is likely that a portion of the endogenous Rac would still contain bound GTP even when 10 μM GTPγS is added. By adding GTPγS to dialyzed cytosol in which endogenous GTP levels have been depleted, nearly all of the Rac present will have bound GTPγS. Under these conditions, NADPH oxidase activity was almost totally resistant to inhibition by p190 GAP (FIG. 3).

The ability of GTPγS to reverse the inhibition by p190 GAP of $O_2^-$ formation suggests that this effect of p190 was due to its ability to stimulate GTP hydrolysis. When a second GAP (CDC42Hs GAP) active on Rac in the cell-free system was tested, inhibition of NADPH oxidase activity in a GTPγS-sensitive fashion was observed. Furthermore, there was an excellent correlation between the relative activity of these two GAPs for stimulating GTP hydrolysis by Rac in vitro and their ability to inhibit NADPH oxidase activity (data not shown). Thus, it was observed that it took approximately 10- to 20-fold more p190 GAP to stimulate a level of Rac GTP hydrolysis equal to that produced by a given amount of CDC42Hs GAP, and it also took 10- to 20-fold more p190 GAP to inhibit $O_2^-$ formation in the cell-free assay.

Rac2 and Rac1 have been shown to support NADPH oxidase activity, while the other members of the Rho family of GTP-binding proteins, Rho and CDC42Hs, are inactive in this system (Mizuno, et al., Id. (1992); Kwong, et al., Id. (1993); Heyworth, et al., Id. (1993)). Since p190 can stimulate GTP hydrolysis by B all members of the Rho family, it was important to be certain that its inhibitory effect on the NADPH oxidase was the result of an action on Rac.

Figure 8:
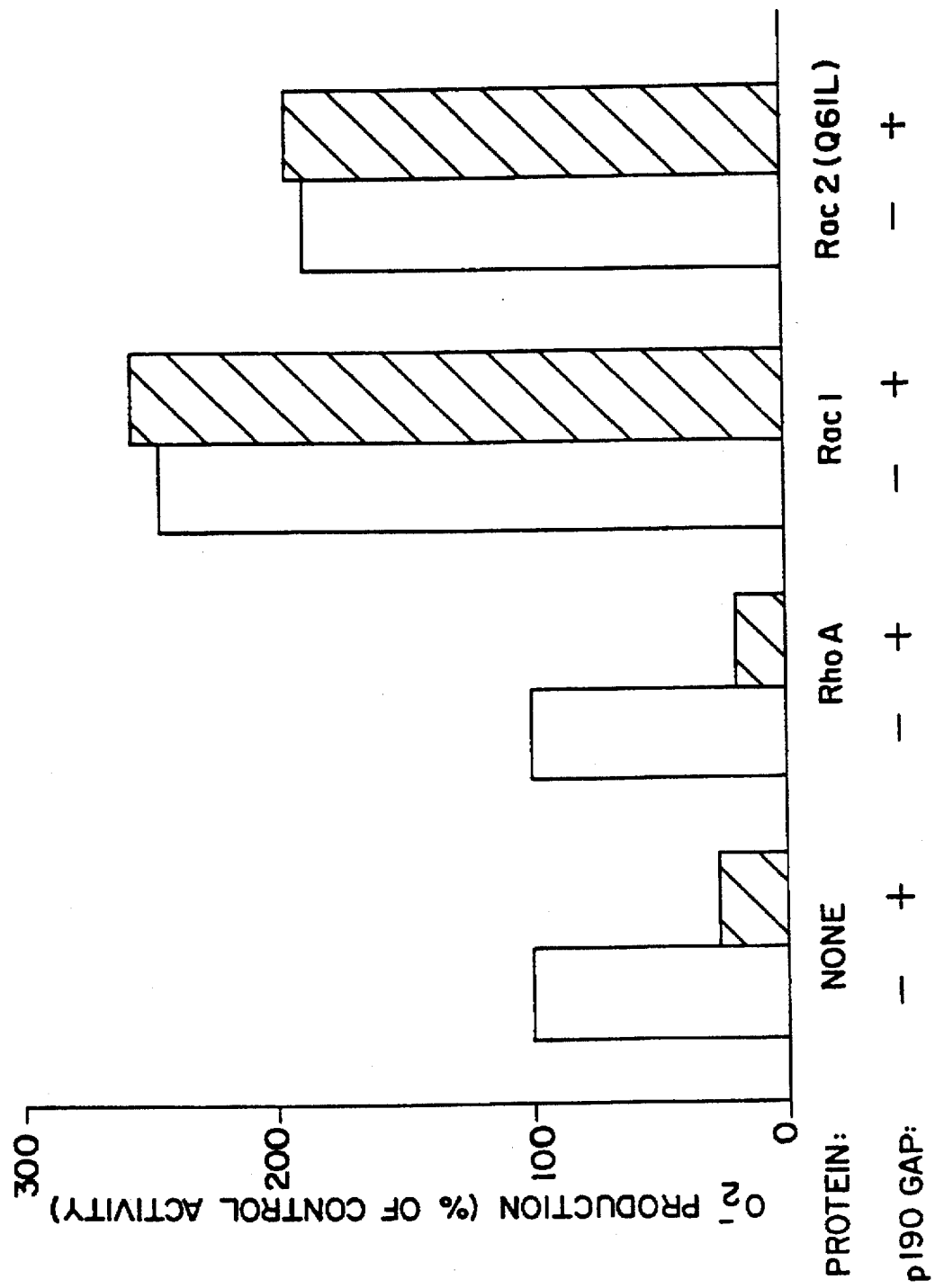
FIG. 8 illustrates that the addition of Rac GTP-binding proteins overcomes p190 GAP inhibition of $O_2^-$ production by NADPH oxidase. On the vertical axis, $O_2^-$ production (% of control activity) is shown, while the bars on the horizontal axis illustrate the results seen in reaction wells containing various amounts and types of protein, in the presence (+) or absence (−) of p190 GAP. Reaction mixtures contained $4 \times 10^5$ cell eq membranes and $1.8 \times 10^6$ cell eq cytosol. In addition, reaction wells were supplemented with Rac1.GTPγS (30 nM), RhoA.GTPγS (100 nM), Rac2 (Q61L, 10 nM), or had no GTP-binding protein added, and contained either no p190 GAP (open bars) or 280 nM p190 GAP (cross-hatched bars), as indicated in the FIGURE. The control rate of $O_2^-$ generation was 30.1±4.3 nmol/min/$10^7$ cell eq membrane. The data shown are representative of at least two experiments.

FIG. 8 shows that the addition to the cell-free assay of a Rac2 (Q61L) mutant protein which does not hydrolyze GTP and is unresponsive to p190 GAP activity (Xu, et al., Id. (1993)) to the cell-free assay was able to overcome totally the inhibitory effects of p190 GAP. Similarly, a GTPγS-loaded Rac1 protein also reversed the inhibitory activity of p190 GAP. In marked contrast, a GTPγS-bound form of RhoA did not reverse inhibition of NADPH oxidase activity by p190, even though this GTP-binding protein interacts even more strongly with p190 (Settleman, et al., Id. (1992)). Both Rac-GTPγS and Rac2-GTP (i.e., the Q61L mutant) caused an increase in the rate of $O_2^-$ production over the control cytosol, suggesting that the level of endogenous Rac protein present was insufficient for maximal stimulation of the NADPH oxidase, perhaps due to the action of endogenous GAPs and other regulatory factors.

The experiments described above suggest that GAP proteins, and particularly p190 GAP, effectively inhibit NADPH oxidase through an effect on the levels of active Rac-GTP. The precise mechanisms through which Rac protein stimulates formation of $O_2^-$ by the NADPH oxidase are still unknown, however. It is likely that formation of the active oxidase involves the assembly of a multiprotein complex consisting minimally of p47phox, p67phox, cytochrome $b_{558}$, and probably involves Rac at the level of the plasma membrane. All of the three required cytosolic factors have been shown to translocate to the plasma membrane upon cell activation (Clark, et al., J. Clin. Invest. 85: 714–721 (1990); Heyworth, et al., J. Clin. Invest. 87: 352–356 (1991)), and membrane association of at least the p47phox and p67phox components is dependent upon cytochrome $b_{558}$ (Heyworth, et al., Id. (1991); Kleinberg, et al., *J. Biol. Chem.* 265: 15577–15583 (1990)). The nature and mechanism of action of this active complex have not yet been defined, however. The Rac protein would appear to be in the active, GTP-bound state at this stage, since Rac must be in a GTP-bound form for oxidase activation to occur (Mizuno, et al., *J. Biol. Chem.* 267: 10215–10218 (1992); Kwong, et al., *Biochemistry* 32: 5711–5717 (1993); Heyworth, et al., *Mol. Biol. Cell* 4: 261–269 (1993)) and GTP binding to Rac may precede the translocation event (Phillips, et al., *Science* 259:977–980 (1993); Bokoch, et al., *FASEB J.* 7:750–759 (1993)).

The susceptibility of Rac to the action of p190 GAP in the active oxidase complex was examined by determining the ability of GAP to inhibit $O_2^-$ formation in the cell-free assay once the reaction had been initiated with SDS. As shown in FIG. 9, after the addition of stimulus to form active oxidase, p190 GAP was no longer able to inhibit $O_2^-$ formation, even when added within 100 seconds of the addition of SDS and before the maximum rate of $O_2^-$ generation was achieved. However, the NADPH oxidase could be inhibited at this stage by the addition of diphenylene iodonium, a potent NADPH oxidase inhibitor (Cross and Jones, *Biochem. J.* 237: 111–116 (1986)). This loss of the inhibitory effect of the Rac GAP when added after oxidase activation suggests either that the GAP no longer has access to Rac in the active, multiprotein complex formed, or that the action of Rac-GTP is no longer necessary once an active enzyme has been established.

D. Discussion

Evidence is provided herein that human neutrophil NADPH oxidase is susceptible to regulation by GAP proteins able to stimulate GTP hydrolysis by Rac. Previous studies have suggested that the oxidase system can be modulated by other proteins known to interact with and regulate the nucleotide state of Rac, including smgGDS and [Rho]GDI. (See Knaus, et al., Id. (1992); Mizuno, et al., Id. (1992); Kwong, et al., Id. (1993); Abo, et al., Id. (1991).) Since GAPs act by stimulating the conversion of GTP to GDP, forming the inactive state of the low molecular weight GTP-binding (LMWG) protein substrate, these data indicate that the GTP-bound form of a small GTP-binding protein is essential for NADPH oxidase activation to occur. This is consistent with previous results which demonstrated that GTP was an absolute requirement of the NADPH oxidase (Uhlinger, et al., *J. Biol. Chem.* 266: 20990–20997 (1991); Peveri, et al., *PNAS USA* 89: 2494–2498 (1992)). The within-disclosed results are also consistent with data from other cell-free studies which indicate that only the GTP-bound form of Rac is active in supporting NADPH oxidase activation. (See, e.g., Mizuno, et al., Id. (1992); Kwong, et al., Id. (1993); Heyworth, et al., Id. (1993); and Abo, et al., id. (1991).)

The GAPs used in the presently-disclosed studies are p190 GAP and CDC42Hs GAP. It was previously suggested that p190 is active on members of the Rho family of GTP-binding proteins (Settleman, et al., Id. (1992)); it has now been found to be active on both Rac1 and Rac2 (see FIG. 7). Similarly, it has now been demonstrated that CDC42Hs GAP is nearly as active with Rac1 and Rac2 as with CDC42Hs (data not shown).

The inhibitory action of p190 on NADPH oxidase was almost certainly due to its ability to stimulate GTP hydrolysis by Rac, as: (1) inhibition was prevented in the presence of the non-hydrolyzable GTP analog, GTPγS (see, e.g., FIG. 7); (2) the degree of inhibition caused by p190 GAP v. CDC42Hs GAP was directly correlated with their relative GAP activity toward Rac (data not shown); and (3) the inhibitory effect of p190 could be reversed by addition of GTP-bound forms of Rac1 and Rac2, but not by the GTPγS-bound form of RhoA (see, e.g., FIG. 8). These data confirm the critical role of Rac in regulating the human phagocyte NADPH oxidase.

p190 is a phosphoprotein that becomes tightly associated with p120 Ras GAP in mitogenically stimulated and tyrosine kinase-transformed cells (Ellis, et al., *Nature* 343: 377–381 (1990)). p190 may therefore provide a link between the Rho signalling pathway and signal transduction pathways regulated by Ras. It has now been shown via immunoblotting that p190 is present in mature human neutrophils and fully DMSO-differentiated HL60 cells. For example, human neutrophil membranes (30 µg) or cytosol (50 µg), and DMSO-differentiated HL60 cell lysates ($2 \times 10^5$ cell eq) were immunoblotted with a 1:1000 dilution of a p190-specific antibody as described hereinabove. Results (not shown) confirmed that p190 is present in human phagocytic leukocytes. Whether p190 serves as a normal physiological regulator of the NADPH oxidase is not yet confirmed, and the presently-disclosed studies allow no definitive conclusions to be drawn in this regard at this time. However, the present studies do establish that p190 is present and indicate that it can regulate the activity of the NADPH oxidase.

The cell-free assay of $O_2^-$ generation is conducted in the presence of 100 µM SDS as an activating stimulus. The levels of p190 required to cause inhibition under these conditions are in the range of 100–400 nM, which correlated well with the concentrations of p190 required to stimulate GTP hydrolysis by Rac in the presence of identical concentrations of SDS (compare FIGS. 3 and 7). Whether p190 is active in intact, stimulated neutrophils, and whether its activity might be regulated by phosphorylation in these cells, remains to be investigated. Rac GAP activity distinct from p190 has now been detected in human neutrophils (data not shown), and these proteins may also be important in determining NADPH oxidase activity, as well as in regulating other functions modulated by Rac, such as actin assembly (Ridley, et al., *Cell* 70: 401–410 (1992)). It will be important in future studies to begin to define the mechanisms by which individual Rac GAPs are regulated during phagocyte activation.

While Rac2 is required for NADPH oxidase activation and is known to translocate from the cytosol to the plasma membrane upon cell activation, the specific role(s) of Rac in regulating the system remain to be determined. Whether Rac participates as a component of the assembled NADPH oxidase along with p47phox, p67phox, and cytochrome $b_{558}$ is not presently known. It has now been observed, however, that Rac was no longer responsive to p190 action once the NADPH oxidase was activated and assembled (see FIG. 9). This could indicate that p190 does not have access to the Rac protein when it is interacting with other oxidase components. Such a hypothesis would be consistent with what is known about Ras structure; in Ras, both GAP and downstream effectors (i.e., Raf kinase) bind to a shared "effector" domain made up of amino acid residues 32–40 (Moodie, et al., *Science* 260: 1658–1661 (1993); Vojtek, et al., *Cell* 74: 205–214 (1993)). Whether the equivalent domain in Rac is important for NADPH oxidase activation has not yet been established. If Rac in the active oxidase is indeed protected from GAP action, then this would suggest that Rac GAP(s) do not serve as the immediate signal for termination of the respiratory burst response.

Alternatively, the inability of p190 to inhibit NADPH oxidase once the system has been stimulated might indicate that the GTP-bound Rac is no longer required to maintain activity of the enzyme once activation has been initiated. While this possibility cannot be ruled out, the observation that Rac translocation is continuous during the time course of oxidase activation by chemoattractants and phorbol esters suggests that continuous activity of Rac is necessary to maintain an active enzyme. Based on current knowledge of GTP-binding protein action, this active Rac is likely to be the GTP-bound form.

Nevertheless, it has now been demonstrated that the human neutrophil NADPH oxidase is subject to negative regulation by proteins, such as p190, which can stimulate GTP hydrolysis by Rac. Thus, the NADPH oxidase appears subject to regulation by each of the three known classes of proteins able to modulate the GTP/GDP state of Ras-related GTP-binding proteins. It is of interest that the activity of certain GAPs may be modulated by the activation of cell surface hormone receptors (Marti and Lapetina, *PNAS USA* 89: 2784–2788 (1992); Liu, et al., *Science* 256: 1456–1458 (1992)), and the possibility that Rac GAP(s) in neutrophils is/are subject to chemoattractant-mediated regulation is a viable one. Rac-GTP appears not to be accessible to p190 after assembly of the active oxidase complex. Thus, the use of a GAP protein capable of modulating the activity of Rac in an intact system provides insight into the structure and function of the phagocyte NADPH oxidase system.

The foregoing is intended to be illustrative of the present invention, but not limiting. Numerous variations and modifications may be effected without departing from the true spirit and scope of the invention. It is further to be understood that the within-disclosed inventions are not limited to or by a particular theory of operation.

We claim:

1. A non-toxic peptide that inhibits superoxide production in phagocytic cells, wherein said peptide
   (a) displays oxidase-inhibitory activity;
   (b) is about 6 to about 20 amino acid residues in length; and
   (c) has an amino acid residue sequence corresponding to that of ICS4 (SEQ ID NO 6) or a fragment thereof.

2. A non-toxic peptide that inhibits superoxide production in phagocytic cells, wherein said peptide
   (a) displays oxidase-inhibitory activity;
   (b) is about 9 to about 20 amino acid residues in length;
   (c) is a fragment of a low molecular weight GTP-binding protein (LMWG); and
   (d) includes a sequence selected from the group consisting of:

GNIFANLFKGLFGkKE (SEQ ID NO7);
GLTISSLFSRLFGKKO (SEQ ID NO8);
TISSLFSRLFGKKO (SEQ ID NO9);
SSLFSRLFGKKO (SEQ ID NO10);
CPPPVKKRKRK (SEQ ID NO11);
CPOPTROOKRA (SEQ ID NO12);
PGKARKKSS (SEQ ID NO13);
EKKKPKKKS (SEQ ID NO14);
LTORGLKTVFDE (SEQ ID NO16):
EKLKEKKLTPI (SEQ ID NO17);

and fragments thereof.

3. A composition that inhibits respiratory burst consisting essentially of a peptide according to claims 1 or 2.

* * * * *